United States Patent [19]

Argyropoulos et al.

[11] Patent Number: 5,932,772
[45] Date of Patent: Aug. 3, 1999

[54] SEPARATION PROCESSES

[75] Inventors: John N. Argyropoulos, Scott Depot; David Robert Bryant, South Charleston; Donald Lee Morrison, Dunbar; Kenneth Elwood Stockman, Charleston; Anthony George Abatjoglou, South Charleston, all of W. Va.

[73] Assignee: Union Carbide Chemicals & Plastics Technology Corporation, Danbury, Conn.

[21] Appl. No.: 09/017,457

[22] Filed: Feb. 2, 1998

[51] Int. Cl.$^6$ .................................................. C07C 45/50
[52] U.S. Cl. ........................... 568/454; 568/451; 560/177; 558/85
[58] Field of Search .................... 568/424, 451; 560/177; 558/71, 85

[56] References Cited

U.S. PATENT DOCUMENTS

| | | | |
|---|---|---|---|
| 4,845,306 | 7/1989 | Puckette | 568/454 |
| 5,138,101 | 8/1992 | Devon | 568/492 |
| 5,180,854 | 1/1993 | Abatjoglou et al. | 568/454 |
| 5,463,082 | 10/1995 | Horvath et al. | 549/46 |
| 5,648,554 | 7/1997 | Mori et al. | 568/454 |
| 5,719,312 | 2/1998 | Hansen | 560/177 |
| 5,789,625 | 8/1998 | Bryant | 568/454 |

FOREIGN PATENT DOCUMENTS 9715543   5/1997   WIPO.

*Primary Examiner*—Shailendra Kumar
*Assistant Examiner*—Sreeni Padmanabhan
*Attorney, Agent, or Firm*—Gerald C. Coon

[57] ABSTRACT

This invention relates to a process for separating one or more products from a reaction product fluid comprising a metal-organophosphorus ligand complex catalyst, optionally free organophosphorus ligand, a polar solvent and said one or more products, wherein said process comprises (1) mixing said reaction product fluid with a nonpolar solvent to obtain by phase separation a polar phase comprising said metal-organophosphorus ligand complex catalyst, optionally free organophosphorus ligand and said polar solvent and a nonpolar phase comprising said one or more products and nonpolar solvent, and (2) recovering said nonpolar phase from said polar phase; wherein said organophosphorus ligand has a partition coefficient between the polar solvent and the nonpolar solvent of greater than about 10, and said one or more products have a partition coefficient between the nonpolar solvent and the polar solvent of greater than about 0.5.

18 Claims, No Drawings

SEPARATION PROCESSES

RELATED APPLICATION

This application is related to copending U.S. patent application Ser. No. 09/017,456, filed on an even date herewith, the disclosure of which is incorporated herein by reference.

BRIEF SUMMARY OF THE INVENTION

1. Technical Field

This invention relates to improved metal-organophosphorus ligand complex catalyzed processes. More particularly this invention relates to metal-organophosphorus ligand complex catalyzed processes in which the desired product can be selectively extracted and separated from the reaction product fluid by phase separation.

2. Background of the Invention

It is known in the art that various products may be produced by reacting one or more reactants in the presence of an metal-organophosphorus ligand complex catalyst. However, stabilization of the catalyst and organophosphorus ligand remains a primary concern of the art. Obviously catalyst stability is a key issue in the employment of any catalyst. Loss of catalyst or catalytic activity due to undesirable reactions of the highly expensive metal catalysts can be detrimental to the production of the desired product. Moreover, production costs of the product obviously increase when productivity of the catalyst decreases.

For instance, a cause of organophosphorus ligand degradation and catalyst deactivation of metal-organophosphorus ligand complex catalyzed hydroformylation processes is due in part to vaporizer conditions present during, for example, in the vaporization employed in the separation and recovery of the aldehyde product from the reaction product mixture. When using a vaporizer to facilitate separation of the aldehyde product of the process, a harsh environment of a high temperature and a low carbon monoxide partial pressure than employed during hydroformylation is created, and it has been found that when a organophosphorus promoted rhodium catalyst is placed under such vaporizer conditions, it will deactivate at an accelerated pace with time. It is further believed that this deactivation is likely caused by the formation of an inactive or less active rhodium species. Such is especially evident when the carbon monoxide partial pressure is very low or absent. It has also been observed that the rhodium becomes susceptible to precipitation under prolonged exposure to such vaporizer conditions.

For instance, it is theorized that under harsh conditions such as exist in a vaporizer, the active catalyst, which under hydroformylation conditions is believed to comprise a complex of rhodium, organophosphorus ligand, carbon monoxide and hydrogen, loses at least some of its coordinated carbon monoxide, thereby providing a route for the formation of such a catalytically inactive or less active rhodium. Accordingly, a successful method for preventing and/or lessening such degradation of the organophosphorus ligand and deactivation of the catalyst as occur under harsh separation conditions in a vaporizer would be highly desirable to the art.

DISCLOSURE OF THE INVENTION

It has now been discovered that in metal-organophosphorus ligand complex catalyzed processes, the desired product can be selectively extracted and separated from the reaction product fluid by phase separation. By the practice of this invention, it is now possible to separate the desired product from the reaction product fluid without the need to use vaporization separation and the harsh conditions associated therewith. This invention provides a highly desirable separation method which prevents and/or lessens degradation of the organophosphorus ligand and deactivation of the catalyst as occur under harsh conditions with vaporization separation.

This invention relates in part to a process for separating one or more products from a reaction product fluid comprising a metal-organophosphorus ligand complex catalyst, optionally free organophosphorus ligand, a nonpolar solvent, a polar solvent and said one or more products, wherein said process comprises (1) mixing said reaction product fluid to obtain by phase separation a polar phase comprising said metal-organophosphorus ligand complex catalyst, optionally free organophosphorus ligand and said polar solvent and a nonpolar phase comprising said one or more products and nonpolar solvent, and (2) recovering said nonpolar phase from said polar phase; wherein said organophosphorus ligand has a partition coefficient between the polar solvent and the nonpolar solvent of greater than about 10, and said one or more products have a partition coefficient between the nonpolar solvent and the polar solvent of greater than about 0.5.

This invention also relates in part to process for separating one or more products from a reaction product fluid comprising a metal-organophosphorus ligand complex catalyst, optionally free organophosphorus ligand, a polar solvent and said one or more products, wherein said process comprises (1) mixing said reaction product fluid with a nonpolar solvent to obtain by phase separation a polar phase comprising said metal-organophosphorus ligand complex catalyst, optionally free organophosphorus ligand and said polar solvent and a nonpolar phase comprising said one or more products and nonpolar solvent, and (2) recovering said nonpolar phase from said polar phase; wherein said organophosphorus ligand has a partition coefficient between the polar solvent and the nonpolar solvent of greater than about 10, and said one or more products have a partition coefficient between the nonpolar solvent and the polar solvent of greater than about 0.5.

This invention further relates in part to a process for producing one or more products comprising: (1) reacting one or more reactants in the presence of a metal-organophosphorus ligand complex catalyst, optionally free organophosphorus ligand, a polar solvent and a nonpolar solvent to form a multiphase reaction product fluid; and (2) separating said multiphase reaction product fluid to obtain one phase comprising said one or more reactants, metal-organophosphorus ligand complex catalyst, optionally free organophosphorus ligand and polar solvent and at least one other phase comprising said one or more products and nonpolar solvent; wherein said organophosphorus ligand has a partition coefficient between the polar solvent and the nonpolar solvent of greater than about 10, and said one or more products have a partition coefficient between the nonpolar solvent and the polar solvent of greater than about 0.5.

This invention yet further relates in part to a process for producing one or more products comprising: (1) reacting one or more reactants in the presence of a metal-organophosphorus; ligand complex catalyst, optionally free organophosphorus ligand and a polar solvent to form a reaction product fluid; (2) mixing said reaction product fluid with a nonpolar solvent to form a multiphase reaction product fluid; and (3) separating said multiphase reaction product fluid to obtain one phase comprising said one or more reactants, metal-organophosphorus ligand complex catalyst, optionally free organophosphorus ligand and polar solvent and at least one other phase comprising said one or more products and nonpolar solvent; wherein said organophosphorus ligand has a partition coefficient between the polar solvent and the nonpolar solvent of greater than about 10, and said one or more products have a partition coefficient between the nonpolar solvent and the polar solvent of greater than about 0.5.

This invention also relates in part to a process for producing aldehydes comprising: (1) reacting an olefinic unsaturated compound with carbon monoxide and hydrogen in the presence of a metal-organophosphorus ligand complex catalyst, optionally free organophosphorus ligand, a polar solvent and a nonpolar solvent to form a multiphase reaction product fluid; and (2) separating said multiphase reaction product fluid to obtain one phase comprising said olefinic unsaturated compound, metal-organophosphorus ligand complex catalyst, optionally free organophosphorus ligand and polar solvent and at least one other phase comprising said aldehydes and nonpolar solvent; wherein organophosphorus ligand has a partition coefficient between the polar solvent and the nonpolar solvent of greater than about 10, and said aldehydes have a partition coefficient between the nonpolar solvent and the polar solvent of greater than about 0.5.

This invention further relates in part to a process for producing aldehydes comprising: (1) reacting an olefinic unsaturated compound with carbon monoxide and hydrogen in the presence of a metal-organophosphorus ligand complex catalyst, optionally free organophosphorus ligand and a polar solvent to form a reaction product fluid; (2) mixing said reaction product fluid with a nonpolar solvent to form a multiphase reaction product fluid; and (3) separating said multiphase reaction product fluid to obtain one phase comprising said olefinic unsaturated compound, metal-organophosphorus ligand complex catalyst, optionally free organophosphorus ligand and polar solvent and at least one other phase comprising said aldehydes and nonpolar solvent; wherein organophosphorus ligand has a partition coefficient between the polar solvent and the nonpolar solvent of greater than about 10, and said aldehydes have a partition coefficient between the nonpolar solvent and the polar solvent of greater than about 0.5.

DETAILED DESCRIPTION

General Processes

The processes of this invention may be asymmetric or non-asymmetric, the preferred processes being non-asymmetric, and may be conducted in any continuous or semi-continuous fashion. The product/catalyst extraction and separation are critical features of this invention and may be conducted as described herein. The processing techniques used in this invention may correspond to any of the known processing techniques heretofore employed in conventional processes. Likewise, the manner or order of addition of the reaction ingredients and catalyst are also not critical and may be accomplished in any conventional fashion. As used herein, the term "reaction product fluid" is contemplated to include, but not limited to, a reaction mixture containing an amount of any one or more of the following: (a) a metal-organophosphorus ligand complex catalyst, (b) free organophosphorus ligand, (c) product(s) formed in the reaction, (d) unreacted reactant(s), and (e) solvent(s).

This invention encompasses the carrying out of known conventional syntheses in a conventional fashion and the carrying out of product/catalyst extractions and separations in accordance with this invention. By the practice of this invention, it is now possible to extract and separate the desired product from the metal-organophosphorus ligand complex catalyst without the need to use vaporization separation and the harsh conditions associated therewith.

Illustrative processes include, for example, hydroformylation, hydroacylation (intramolecular and intermolecular), hydrocyanation, hydroamidation, hydroesterification, aminolysis, alcoholysis, hydrocarbonylation, hydroxycarbonylation, carbonylation, olefin isomerization, transfer hydrogenation and the like. Preferred processes involve the reaction of organic compounds with carbon monoxide, or with carbon monoxide and a third reactant, e.g., hydrogen, or with hydrogen cyanide, in the presence of a catalytic amount of a metal-organophosphorus ligand complex catalyst. The most preferred processes include hydroformylation, hydrocyanation, hydrocarbonylation, hydroxycarbonylation and carborlylation.

Hydroformylation can be carried out in accordance with conventional procedures known in the art. For example, aldehydes can be prepared by reacting an olefinic compound, carbon monoxide and hydrogen under hydroformylation conditions in the presence of a metal-organophosphorus ligand complex catalyst described herein. Alternatively, hydroxyaldehydes can be prepared by reacting an epoxide, carbon monoxide and hydrogen under hydroformylation conditions in the presence of a metal-organophosphorus ligand complex catalyst described herein. The hydroxyaldehyde can be hydrogenated to a diol, e.g., hydroxypropionaldehyde can be hydrogenated to propanediol. Hydroformylation processes are described more fully hereinbelow.

Intramolecular hydroacylation can be carried out in accordance with conventional procedures known in the art. For example, aldehydes containing an olefinic group 3 to 7 carbons removed can be converted to cyclic ketones under hydroacylation conditions in the presence of a metal-organophosphorus ligand complex catalyst described herein.

Intermolecular hydroacylation can be carried out in accordance with conventional procedures known in the art. For example, ketones can be prepared by reacting an olefin and an aldehyde under hydroacylation conditions in the presence of a metal-organophosphorus ligand complex catalyst described herein.

Hydrocyanation can be carried out in accordance with conventional procedures known in the art. For example, nitrile compounds can be prepared by reacting an olefinic compound and hydrogen cyanide under hydrocyanation conditions in the presence of a metal-organophosphorus ligand complex catalyst described herein. A preferred hydrocyanation process involves reacting a nonconjugated acyclic aliphatic monoolefin, a monoolefin connected to an ester group, e.g., methyl pent-2-eneoate, or a monoolefin conjugated to a nitrile group, e.g., 3-pentenenitrile, with a source of hydrogen cyanide in the presence of a catalyst precursor composition comprising zero-valent nickel and a bidentate phosphite ligand to produce a terminal organonitrile, e.g., adiponitrile, alkyl 5-cyanovalerate or 3-(perfluoroalkyl) propionitrile. Preferably, the reaction is carried out in the presence of a Lewis acid promoter. Illustrative hydrocyanation processes are disclosed in U.S. Pat. No. 5,523,453 and WO 95/14659, the disclosures of which are incorporated herein by reference.

Hydroamidation can be carried out in accordance with conventional procedures known in the art. For example, amides can be prepared by reacting an olefin, carbon monoxide and a primary or secondary amine or ammonia under hydroamidation conditions in the presence of a metal-organophosphorus ligand complex catalyst described herein.

Hydroesterification can be carried out in accordance with conventional procedures known in the art. For example, esters can be prepared by reacting an olefin, carbon monoxide and an alcohol under hydroesterification conditions in the presence of a metal-organophosphorus ligand complex catalyst described herein.

Aminolysis can be carried out in accordance with conventional procedures known in the art. For example, amines can be prepared by reacting an olefin with a primary or secondary amine under aminolysis conditions in the presence of a metal-organophosphorus ligand complex catalyst described herein.

Alcoholysis can be carried out in accordance with conventional procedures known in the art. For example, ethers can be prepared by reacting an olefin with an alcohol under alcoholysis conditions in the presence of a metal-organophosphorus ligand complex catalyst described herein.

Hydrocarbonylation can be carried out in accordance with conventional procedures known in the art. For example, alcohols can be prepared by reacting an olefinic compound, carbon monoxide, hydrogen and a promoter under hydrocarbonylation conditions in the presence of a metal-organophosphorus ligand complex catalyst described herein.

Hydroxycarbonylation can be carried out in accordance with conventional procedures known in the art. For example, acids can be prepared by reacting an olefinic compound, carbon monoxide, water and a promoter under hydroxycarbonylation conditions in the presence of a metal-organophosphorus ligand complex catalyst described herein.

Carbonylation can be carried out in accordance with conventional procedures known in the art. For example, lactones can be prepared by treatment of allylic alcohols with carbon monoxide under carbonylation conditions in the presence of a metal-organophosphorus ligand complex catalyst described herein.

Isomerization can be carried out in accordance with conventional procedures known in the art. For example, allylic alcohols can be isomerized under isomerization conditions to produce aldehydes in the presence of a metal-organophosphorus ligand complex catalyst described herein.

Transfer hydrogenation can be carried out in accordance with conventional procedures known in the art. For example, alcohols can be prepared by reacting a ketone and an alcohol under transfer hydrogenation conditions in the presence of a metal-organophosphorus ligand complex catalyst described herein.

The permissible starting material reactants encompassed by the processes of this invention are, of course, chosen depending on the particular process desired. Such starting materials are well known in the art and can be used in conventional amounts in accordance with conventional methods. Illustrative starting material reactants include, for example, substituted and unsubstituted aldehydes, (intramolecular hydroacylation), olefins (hydroformylation, carbonylaltion, intermolecular hydroacylation, hydrocyanation, hydroamidation, hydroesterification, aminolysis, alcoholysis), ketones (transfer hydrogenation), epoxides (hydroformylation, hydrocyanation), alcohols (carbonylation) and the like. Illustrative of suitable reactants for effecting the processes of this invention are set out in Kirk-Othmer, Encyclopedia of Chemical Technology, Fourth Edition, 1996, the pertinent portions of which are incorporated herein by reference.

Illustrative metal-organophosphorus ligand complex catalysts employable in the processes encompassed by this invention as well as methods for their preparation are well known in the art and include those disclosed in the below mentioned patents. In general such catalysts may be preformed or formed in situ as described in such references and consist essentially of metal in complex combination with an organophosphorus ligand. The active species may also contain carbon monoxide and/or hydrogen directly bonded to the metal.

The catalyst useful in the processes includes a metal-organophosphorus ligand complex catalyst which can be optically active or non-optically active. The permissible metals, which make up the metal-organophosphorus ligand complexes included Group 8, 9 and 10 metals selected from rhodium (Rh), cobalt (Co), iridium (Ir), ruthenium (Ru), iron (Fe), nickel (Ni), palladium (Pd), platinum (Pt), osmium (Os) and mixtures thereof, with the preferred metals being rhodium, cobalt, iridium and ruthenium, more preferably rhodium, cobalt and ruthenium, especially rhodium. Other permissible metals include Group 11 metals selected from copper (Cu), silver (Ag), gold (Au) and mixtures thereof, and also Group 6 metals selected from chromium (Cr), molybdenum (Mo), tungsten (W) and mixtures thereof. Mixtures of metals from Groups 6, 8, 9, 10 and 11 may also be used in this invention. The permissible organophosphorus ligands which make up the metal-organophosphorus ligand complexes and free organophosphorus ligand include organophosphines, e.g., bisphosphines and triorganophosphines, and organophosphites, e.g., mono-, di-, tri- and polyorganophosphites. Other permissible organophosphorus ligands include, for example, orgarnophosphonites, organophosphinites, organophosphorus amides and the like. Mixtures of such ligands may be employed if desired in the metal-organophosphorus ligand complex catalyst and/or free ligand and such mixtures may be the same or different. This invention is not intended to be limited in any manner by the permissible organophosphorus ligands or mixtures thereof. It is to be noted that the successful practice of this invention does not depend and is not predicated on the exact structure of the metal-organophosphorus ligand complex species, which may be present in their mononuclear, dinuclear and/or higher nuclearity forms. Indeed, the exact structure is not known. Although it is not intended herein to be bound to any theory or mechanistic discourse, it appears that the catalytic species may in its simplest form consist essentially of the metal in complex combination with the organophosphorus ligand and carbon monoxide and/or hydrogen when used.

The term "complex" as used herein and in the claims means a coordination compound formed by the union of one or more electronically rich molecules or atoms capable of independent existence with one or more electronically poor molecules or atoms, each of which is also capable of independent existence. For example, the organophosphorus ligands employable herein may possess one or more phosphorus donor atoms, each having one available or unshared pair of electrons which are each capable of forming a coordinate covalent bond independently or possibly in concert (e.g., via chelation) with the metal. Carbon monoxide (which is also properly classified as a ligand) can also be present and complexed with the metal. The ultimate composition of the complex catalyst may also contain an additional ligand, e.g., hydrogen or an anion satisfying the coordination sites or nuclear charge of the metal. Illustrative additional ligands include, for example, halogen (Cl, Br, I), alkyl, aryl, substituted aryl, acyl, $CF_3$, $C_2F_5$, CN, $(R)_2PO$ and RP(O)(OH)O (wherein each R is, the same or different and is a substituted or unsubstituted hydrocarbon radical, e.g., the alkyl or aryl), acetate, acetylacetonate, SO$_4$, PF$_4$, PF$_6$, NO$_2$, NO$_3$, CH$_3$O, CH$_2$=CHCH$_2$, CH$_3$CH=CHCH$_2$, C$_6$H$_5$CN, CH$_3$CN, NO, NH$_3$, pyridine, (C$_2$H$_5$)$_3$N, monoolefins, diolefins and triolefins, tetrahydrofuran, and the like. It is of course to be understood that the complex species are preferably free of any additional organic ligand or anion that might poison the catalyst or have an undue adverse effect on catalyst performance. It is preferred in the metal-organophosphorus ligand complex catalyzed processes, e.g., hydroformylation, that the active catalysts be free of halogen and sulfur directly bonded to the metal, although such may not be absolutely necessary. Preferred complexes include neutral metal complexes in which the central metal and its surrounding ligands form a neutral species. These neutral metal complexes should be distinguished from ionic metal complexes of the type described in WO 97/15543, published May 1, 1997. Preferred metal-ligand complex catalysts include rhodium-organophosphine ligand complex catalysts and rhodium-organophosphite ligand complex catalysts.

The number of available coordination sites on such metals is well known in the art. Thus the catalytic species may comprise a complex catalyst mixture, in their monomeric, dimeric or higher nuclearity forms, which are preferably characterized by at least one organophosphorus-containing molecule complexed per one molecule of metal, e.g., rhodium. For instance, it is considered that the catalytic species of the preferred catalyst employed in a hydroformylation reaction may be complexed with carbon monoxide and hydrogen in addition to the organophosphorus ligands in view of the carbon monoxide and hydrogen gas employed by the hydroformylation reaction.

The organophosphines and organophosphites that may serve as the ligand of the metal-organophosphorus ligand complex catalyst and/or free ligand of the processes of this invention may be of the achiral (optically inactive) or chiral (optically active) type and are well known in the art. By "free ligand" is meant ligand that is not complexed with (tied to or bound to) the metal, e.g., metal atom, of the complex catalyst. As noted herein, the processes of this invention and especially the hydroformylation process may be carried out in the presence of free organophosphorus ligand. Achiral organophosphines and organophosphites are preferred.

Among the organophosphines that may serve as the ligand of the metal-organophosphine complex catalyst and/or free organophosphine ligand of the reaction mixture starting materials are triorganophosphines, trialkylphosphines, alkyldiarylphosphines, dialkylarylphosphines, dicycloalkylarylphosphines, cycloalkyldiarylphosphines, triaralkylphosphines, trialkarylphosphines, tricycloalkylphosphines, and triarylphosphines, alkyl and/or aryl bisphosphines and bisphosphine mono oxides, and the like. Of course any of the hydrocarbon radicals of such tertiary non-ionic organophosphines may be substituted if desired, with any suitable substituent that does not unduly adversely affect the desired result of the hydroformylation reaction. The organophosphine ligands employable in the reactions and/or methods for their preparation are known in the art. Certain ionic organophosphines such as monosubstituted ionic organophosphines undergo scrambling in which substituents exchange resulting in a mixture of ionic organophosphines undesirable for phase separation. For purposes of this invention, the organophosphine ligand is other than an ionic organophosphine ligand.

Illustrative triorganophosphine ligands may be represented by the formula:

(I)

wherein each $R^1$ is the same or different and is a substituted or unsubstituted monovalent hydrocarbon radical, e.g., an alkyl or aryl radical. Suitable hydrocarbon radicals may contain from 1 to 24 carbon atoms or greater. Illustrative substituent groups that may be present on the aryl radicals include, for example, alkyl radicals, alkoxy radicals, silyl radicals such as —Si($R^2$)$_3$; amino radicals such as —N($R^2$)$_2$; acyl radicals such as —C(O)$R^2$; carboxy radicals such as —C(O)O$R^2$; acyloxy radicals such as —OC(O)$R^2$; amido radicals such as —C(O)N($R^2$)$_2$ and —N($R^2$)C(O)$R^2$; sulfonyl radicals such as —SO$_2R^2$; ether radicals such as —O$R^2$; sulfinyl radicals such as —SO$R^2$; sulfinyl radicals such as —S$R^2$ as well as halogen, nitro, cyano, trifluoromethyl and hydroxy radicals, and the like, wherein each $R^2$ individually represents the same or different substituted or unsubstituted monovalent hydrocarbon radical, with the proviso that in amino substituents such as —N($R^2$)$_2$, each $R^2$ taken together can also represent a divalent bridging group that forms a heterocyclic radical with the nitrogen atom and in amido substituents such as C(O)N($R^2$)$_2$ and —N($R^2$)C(O)$R^2$ each —$R^2$ bonded to N can also be hydrogen. Illustrative alkyl radicals include, for example, methyl, ethyl, propyl, butyl and the like. Illustrative aryl radicals include, for example, phenyl, naphthyl, diphenyl, fluorophenyl, difluorophenyl, benzoyloxyphenyl, carboethoxyphenyl, acetylphenyl, ethoxyphenyl, phenoxyphenyl, hydroxyphenyl; carboxyphenyl, trifluoromethylphenyl, methoxyethylphenyl, acetamidophenyl, dimethylcarbamylphenyl, tolyl, xylyl, and the like.

Illustrative specific organophosphines include, for example, triphenylphosphine, tris-p-tolyl phosphine, tris-p-methoxyphenylphosphine, tris-p-fluorophenylphosphine, tris-p-chlorophenylphosphine, tris-dimethylaminophenylphosphine, propyldiphenylphosphine, t-butyldiphenylphosphine, n-butyldiphenylphosphine, n-hexyldiphenylphosphine, cyclohexyldiphenylphosphine, dicyclohexylphenylphosphine, tricyclohexylphosphine, tribenzylphosphine as well as the alkali and alkaline earth metal salts of sulfonated triphenylphesphines, for example, of (tri-m-sulfophenyl)phosphine and of (m-sulfophenyl) diphenyl-phosphine and the like.

More particularly, illustrative metal-organophosphine complex catalysts and illustrative free organophosphine ligands include, for example, those disclosed in U.S. Pat. Nos. 3,527,809; 4,148,830; 4,247,486; 4,283,562; 4,400, 548; 4,482,749 and 4,861,918, the disclosures of which are incorporated herein by reference.

Among the organophosphites that may serve as the ligand of the metal-organophosphite complex catalyst and/or free organophosphite ligand of the reaction mixture starting materials are monoorganophosphites, diorganophosphites, triorganophosphites and organopolyphosphites. The organophosphite ligands employable in this invention and/or methods for their preparation are known in the art.

Representative monoorganophosphites may include those having the formula:

 (II)

wherein R³ represents a substituted or unsubstituted trivalent hydrocarbon radical containing from 4 to 40 carbon atoms or greater, such as trivalent acyclic and trivalent cyclic radicals, e.g., trivalent alkylene radicals such as those derived from 1,2,2-trimethylolpropane and the like, or trivalent cycloalkylene radicals such as those derived from 1,3,5-trihydroxycyclohexane, and the like. Such monoorganophosphites may be found described in greater detail, for example, in U.S. Pat. No. 4,567,306, the disclosure of which is incorporated herein by reference.

Representative diorganophosphites may include those having the formula:

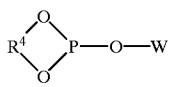 (III)

wherein R⁴ represents a substituted or unsubstituted divalent hydrocarbon radical containing from 4 to 40 carbon atoms or greater and W represents a substituted or unsubstituted monovalent hydrocarbon radical containing from 1 to 18 carbon atoms or greater.

Representative substituted and unsubstituted monovalent hydrocarbon radicals represented by W in the above formula (III) include alkyl and aryl radicals, while representative substituted and unsubstituted divalent hydrocarbon radicals represented by R⁴ include divalent acyclic radicals and divalent aromatic radicals. Illustrative divalent acyclic radicals include, for example, alkylene, alkylene-oxy-alkylene, alkylene-NX-alkylene wherein X is hydrogen or a substituted or unsubstituted monovalent hydrocarbon radical, alkylene-S-alkylene, and cycloalkylene radicals, and the like. The more preferred divalent acyclic radicals are the divalent alkylene radicals such as disclosed more fully, for example, in U.S. Pat. Nos. 3,415,906 and 4,567,302 and the like, the disclosures of which are incorporated herein by reference. Illustrative divalent aromatic radicals include, for example, arylene, bisarylene, arylene-alkylene, arylene-alkylene-arylene, arylene-oxy-arylene, arylene-NX-arylene wherein X is as defined above, arylene-S-arylene, and arylene-S-alkylene, and the like. More preferably R⁴ is a divalent aromatic radical such as disclosed more fully, for example, in U.S. Pat. Nos. 4,599,206 and 4,717,775, and the like, the disclosures of which are incorporated herein by reference.

Representative of a more preferred class of diorganophosphites are those of the formula:

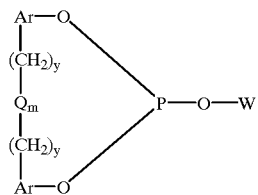 (IV)

wherein W is as defined above, each Ar is the same or different and represents a substituted or unsubstituted aryl radical, each y is the same or different and is a value of 0 or 1, Q represents, a divalent bridging group selected from —C(R⁵)₂—, —O—, —S—, —NR⁶—, Si(R⁷)₂— and —CO—, wherein each R⁵ is the same or different and represents hydrogen, alkyl radicals having from 1 to 12 carbon atoms, phenyl, tolyl, and anisyl, R⁶ represents hydrogen or a methyl radical, each R⁷ is the same or different and represents hydrogen or a methyl radical, and m is a value of 0 or 1. Such diorganophosphites are described in greater detail, for example, in U.S. Pat. Nos. 4,599,206, 4,717,775 and 4,835,299, the disclosures of which are incorporated herein by reference.

Representative triorganophosphites may include those having the formula:

 (V)

wherein each R⁸ is the same or different and is a substituted or unsubstituted monovalent hydrocarbon radical e.g., an alkyl, cycloalkyl, aryl, alkaryl and aralkyl radicals which may contain from 1 to 24 carbon atoms. Suitable hydrocarbon radicals may contain from 1 to 24 carbon atoms or greater and may include those described above for R¹ in formula (I). Illustrative triorganophosphites include, for example, trialkyl phosphites, dialkylaryl phosphites, alkyldiaryl phosphites, triaryl phosphites, and the like, such as, for example, trimethyl phosphite, triethyl phosphite, butyldiethyl phosphite, tri-n-propyl phosphite, tri-n-butyl phosphite, tri-2-ethylhexyl phosphite, tri-n-octyl phosphite, tri-n-dodecyl phosphite, dimethylphenyl phosphite, diethylphenyl phosphite, methyldiphenyl phosphite, ethyldiphenyl phosphite, triphenyl phosphite, trinaphthyl phosphite, bis(3,6,8-tri-t-butyl-2-naphthyl)methylphosphite, bis(3,6,8-tri-t-butyl-2-naphthyl)cyclohexylphosphite, tris(3,6-di-t-butyl-2-naphthyl)phosphite, bis(3,6,8-tri-t-butyl-2-naphthyl)(4-biphenyl)phosphite, bis(3,6,8-tri-t-butyl-2-naphthyl)phenylphosphite, bis(3,6,8-tri-t-butyl-2-naphthyl)(4-benzoylphenyl)phosphite, bis(3,6,8-tri-t-butyl-2-naphthyl)(4-sulfonylphenyl)phosphite, and the like. The most preferred triorganophosphite is triphenylphosphite. Such triorganophosphites are described in greater detail, for example, in U.S. Pat. Nos. 3,527,809 and 5,277,532, the disclosures of which are incorporated herein by reference.

Representative organopolyphosphites contain two or more tertiary (trivalent) phosphorus atoms and may include those having the formula:

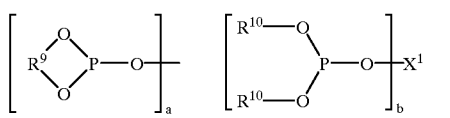
(VI)

wherein $X^1$ represents a substituted or unsubstituted n-valent hydrocarbon bridging radical containing from 2 to 40 carbon atoms, each $R^9$ is the same or different and is a divalent hydrocarbon radical containing from 4 to 40 carbon atoms, each $R^{10}$ is the same or different and is a substituted or unsubstituted monovalent hydrocarbon radical containing from 1 to 24 carbon atoms, a and b can be the same or different and each have a value of 0 to 6, with the proviso that the sum of a+b is 2 to 6 and n equals a+b. Of course it is to be understood that when a has a value of 2 or more, each $R^9$ radical may be the same or different, and when b has a value of 1 or more, each $R^{10}$ radical may also be the same or different.

Representative n-valent (preferably divalent) hydrocarbon bridging radicals represented by $X^1$, as well as representative divalent hydrocarbon radicals represented by $R^9$ above, include both acyclic radicals and aromatic radicals, such as alkylene, alkylene-$Q_m$-alkylene, cycloalkylene, arylene, bisarylene, arylene-alkylene, and arylene-$(CH_2)_y$-$Q_m$-$(CH_2)_y$-arylene radicals, and the like, wherein Q, m and y are as defined above for formula (IV). The more preferred acyclic radicals represented by $X^1$ and $R^9$ above are divalent alkylene radicals, while the more preferred aromatic radicals represented by $X^1$ and $R^9$ above are divalent arylene and bisarylene radicals, such as disclosed more fully, for example, in U.S. Pat. Nos. 4,769,498; 4,774,361: 4,885,401; 5,179,055; 5,113,022; 5,202,297; 5,235,113; 5,264,616 and 5,364,950, and European Patent Application Publication No. 662,468, and the like, the disclosures of which are incorporated herein by reference. Representative monovalent hydrocarbon radicals represented by each $R^{10}$ radical above include alkyl and aromatic radicals.

Illustrative preferred organopolyphosphites may include bisphosphites such as those of formulas (VII) to (IX) below:

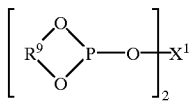
(VII)

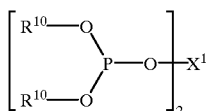
(VIII)

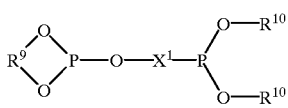
(IX)

wherein each $R^9$, $R^{10}$ and $X^1$ of formulas (VII) to (IX) are the same as defined above for formula (VI). Preferably, each $R^9$ and $X^1$ represents a divalent hydrocarbon radical selected from alkylene, arylene, arylene-alkylene-arylene, and bisarylene, while each $R^{10}$ represents a monovalent hydrocarbon radical selected from alkyl and aryl radicals. Organophosphite ligands of such Formulas (VI) to (IX) may be found disclosed, for example, in U.S. Pat. Nos. 4,668,651; 4,748,261; 4,769,498; 4,774,361; 4,885,401; 5,113,022; 5,179,055; 5,202,297; 5,235,113; 5,254,741; 5,264,616; 5,312,996; 5,364,950; and 5,391,801; the disclosures of all of which are incorporated herein by reference.

Representative of more preferred classes of organobisphosphites are those of the following formulas (X) to (XII):

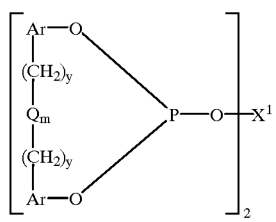
(X)

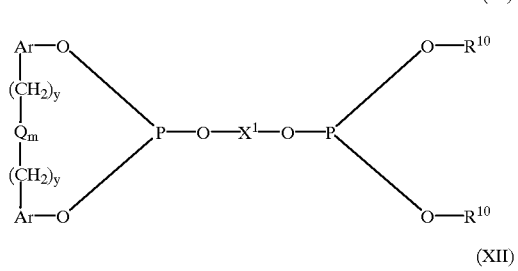
(XI)

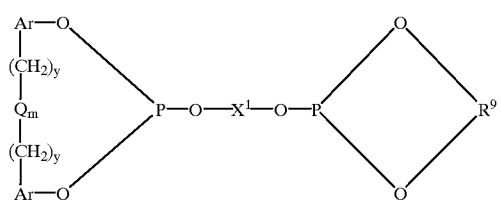
(XII)

wherein Ar, Q, $R^9$, $R^{10}$, $X^1$, m and y are as defined above. Most preferably $X^1$ represents a divalent aryl—$(CH_2)_y$—$(Q)_m$—$(CH_2)_y$—aryl radical wherein each y individually has a value of 0 or 1; m has a value of 0 or 1 and Q is —O—, —S— or —$C(R^5)_2$— wherein each $R^5$ is the same or different and represents a hydrogen or methyl radical. More preferably each alkyl radical of the above defined $R^{10}$ groups may contain from 1 to 24 carbon atoms and each aryl radical of the above-defined Ar, $X^1$, $R^9$ and $R^{10}$ groups of the above formulas (VI) to (XII) may contain from 6 to 18 carbon atoms and said radicals may be the same or different, while the preferred alkylene radicals of $X^1$ may contain from 2 to 18 carbon atoms and the preferred alkylene radicals of $R^9$ may contain from 5 to 18 carbon atoms. In addition, preferably the divalent Ar radicals and divalent aryl radicals of $X^1$ of the above formulas are phenylene radicals in which the bridging group represented by —$(CH_2)_y$—$(Q)_m$—$(CH_2)_y$— is bonded to said phenylene radicals in positions that are ortho to the oxygen atoms of the formulas that connect the phenylene radicals to their phosphorus atom of the formulae. It is also preferred that any substituent radical when present on such phenylene radicals be bonded in the para and/or ortho position of the phenylene radicals in relation to the oxygen atom that bonds the given substituted phenylene radical to its phosphorus atom.

Of course any of the $R^3$, $R^4$, $R^8$, $R^9$, $R^{10}$, $X^1$, $X^2$, W, Q and Ar radicals of such organophosphites of formulas (II) to (XII) above may be substituted if desired, with any suitable substituent containing from 1 to 30 carbon atoms that does not unduly adversely affect the desired result of the hydroformylation reaction. Substituents that may be on said radicals in addition of course to corresponding hydrocarbon radicals such as alkyl, aryl, aralkyl, alkaryl and cyclohexyl substituents, may include for example silyl radicals such as —Si(R$^{12}$)$_3$; amino radicals such as —N(R$^{12}$)$_2$; phosphine radicals such as —aryl—P(R$^{12}$)$_2$; acyl radicals such as —C(O)R$^{12}$; acyloxy radicals such as —OC(O)R$^{12}$; amido radicals such as —CON(R$^{12}$)$_2$ and —N(R$^{12}$)COR$^{12}$; sulfonyl radicals such as —SO$_2$R$^{12}$; alkoxy radicals such as —OR$^{12}$; sulfinyl radicals such as —SOR$^{12}$; sulfinyl radicals such as —SR$^{12}$; phosphonyl radicals such as —P(O)(R$^{12}$)$_2$; as well as, halogen, nitro, cyano, trifluoromethyl, hydroxy radicals, and the like, wherein each R$^{12}$ radical is the same or different and represents a monovalent hydrocarbon radical having from 1 to 18 carbon atoms (e.g., alkyl, aryl, aralkyl, alkaryl and cyclohexyl radicals), with the proviso that in amino substituents such as —N(R$^{12}$)$_2$ each R$^{12}$ taken together can also represent a divalent bridging group that forms a heterocyclic radical with the nitrogen atom, and in amido substituents such as —C(O)N(R$^{12}$)$_2$ and —N(R$^{12}$)COR$^{12}$ each R$^{12}$ bonded to N can also be hydrogen. Of course it is to be understood that any of the substituted or unsubstituted hydrocarbon radicals groups that make up a particular given organophosphite may be the same or different.

More specifically illustrative substituents include primary, secondary and tertiary alkyl radicals such as methyl, ethyl, n-propyl, isopropyl, butyl, sec-butyl, t-butyl, neo-pentyl, n-hexyl, amyl, sec-amyl, t-amyl, iso-octyl, decyl, octadecyl, and the like; aryl radicals such as phenyl, naphthyl and the like; aralkyl radicals such as benzyl, phenylethyl, triphenylmethyl, and the like; alkaryl radicals such as tolyl, xylyl, and the like; alicyclic radicals such as cyclopentyl, cyclohexyl, 1-methylcyclohexyl, cyclooctyl, cyclohexylethyl, and the like; alkoxy radicals such as methoxy, ethoxy, propoxy, t-butoxy, —OCH$_2$CH$_2$OCH$_3$, —(OCH$_2$CH$_2$)$_2$OCH$_3$, —(OCH$_2$CH$_2$)$_3$OCH$_3$, and the like; aryloxy radicals such as phenoxy and the like; as well as silyl radicals such as —Si(CH$_3$)$_3$, —Si(OCH$_3$)$_3$, —Si(C$_3$H$_7$)$_3$, and the like; amino radicals such as —NH$_2$, —N(CH$_3$)$_2$, —NHCH$_3$, —NH(C$_2$H$_5$), and the like; arylphosphine radicals such as —P(C$_6$H$_5$)$_2$, and the like; acyl radicals such as —C(O)CH$_3$, —C(O)C$_2$H$_5$, —C(O)C$_6$H$_5$, and the like; carbonyloxy radicals such as —C(O)OCH$_3$ and the like; oxycarbonyl radicals such as —O(CO)C$_6$H$_5$, and the like; amido radicals such as —CONH$_2$, —CON(CH$_3$)$_2$, —NHC(O)CH$_3$, and the like; sulfonyl radicals such as —S(O)$_2$C$_2$H$_5$ and the like; sulfinyl radicals such as —S(O)CH$_3$ and the like; sulfenyl radicals such as —SCH$_3$, —SC$_2$H$_5$, —SC$_6$H$_5$, and the like; phosphonyl radicals such as —P(O)(C$_6$H$_5$)$_2$, —P(O)(CH$_3$)$_2$, —P(O)(C$_2$H$_5$)$_2$, —P(O)(C$_3$H$_7$)$_2$, —P(O)(C$_4$H$_9$)$_2$, —P(O)(C$_6$H$_{13}$)$_2$, —P(O)CH$_3$(C$_6$H$_5$), —P(O)(H)(C$_6$H$_5$), and the like.

Specific illustrative examples of organophosphorus ligands are described in copending U.S. patent application Ser. No. 08/757,743, filed Nov. 26, 1996, the disclosure of which is incorporated herein by reference.

The metal-organophosphorus ligand complex catalysts are preferably in homogeneous form. For instance, preformed rhodium hydrido-carbonyl-organophosphorus ligand catalysts may be prepared and introduced into the reaction mixture of a particular process. More preferably, the metal-organophosphorus ligand complex catalysts can be derived from a rhodium catalyst precursor which may be introduced into the reaction medium for in situ formation of the active catalyst. For example, rhodium catalyst precursors such as rhodium dicarbonyl acetylacetonate, Rh$_2$O$_3$, Rh$_4$(CO)$_{12}$, Rh$_6$(CO)$_{16}$, Rh(NO$_3$)$_3$ and the like may be introduced into the reaction mixture along with the organophosphorus ligand for the in situ formation of the active catalyst.

As noted above, the organophosphorus ligands can be employed as both the ligand of the metal-organophosphorus ligand complex catalyst, as well as, the free organophosphorus ligand that can be present in the reaction medium of the processes of this invention. In addition, it is to be understood that while the organophosphorus ligand of the metal-organophosphorus ligand complex catalyst and any excess free organophosphorus ligand preferably present in a given process of this invention are normally the same type of ligand, different types of organophosphorus ligands, as well as, mixtures of two or more different organophosphorus ligands may be employed for each purpose in any given process, if desired.

The amount of metal-organophosphorus ligand complex catalyst present in the reaction medium of a given process of this invention need only be that minimum amount necessary to provide the given metal concentration desired to be employed and which will furnish the basis for at least that catalytic amount of metal necessary to catalyze the particular process desired. In general, metal concentrations in the range of from about 1 part per million to about 10,000 parts per million, calculated as free metal, and ligand to metal mole ratios in the catalyst solution ranging from about 1:1 or less to about 200:1 or greater, should be sufficient for most processes.

As noted above, in addition to the metal-organophosphorus ligand complex catalysts, the processes of this invention and especially the hydroformylation process can be carried out in the presence of free organophosphorus ligand. While the processes of this invention may be carried out in any excess amount of free organophosphorus ligand desired, the employment of free organophosphorus ligand may not be absolutely necessary. Accordingly, in general, amounts of ligand of from about 1.1 or less to about 200, or higher if desired, moles per mole of metal. (e.g., rhodium) present in the reaction medium should be suitable for most purposes, particularly with regard to rhodium catalyzed hydroformylation; said amounts of ligand employed being the sum of both the amount of ligand that is bound (complexed) to the metal present and the amount of free (non-complexed) ligand present. Of course, if desired, make-up ligand can be supplied to the reaction medium of the process, at any time and in any suitable manner, to maintain a predetermined level of free ligand in the reaction medium.

The permissible reaction conditions employable in the processes of this invention are, of course, chosen depending on the particular syntheses desired. Such process conditions are well known in the art. All of the processes of this invention can be carried out in accordance with conventional procedures known in the art. Illustrative reaction conditions for conducting the processes of this invention are described, for example, in Kirk-Othmer, Encyclopedia of Chemical Technology, Fourth Edition, 1996, the pertinent portions of which are incorporated herein by reference. Depending on the particular process, operating temperatures may range from about −80° C. or less to about 500° C. or greater and operating pressures can range from about 1 psig or less to about 10,000 psig or greater.

The processes of this invention are conducted for a period of time sufficient to produce the desired products. The exact reaction time employed is dependent, in part, upon factors such as temperature, pressure, nature and proportion of starting materials, and the like. The reaction time will normally be within the range of from about one-half to about 200 hours or more, and preferably from less than about one to about 10 hours.

The processes of this invention are useful for preparing substituted and unsubstituted optically active and non-optically active compounds. Illustrative compounds prepared by the processes of this invention include, for example, substituted and unsubstituted alcohols or phenols; amines; amides; ethers or epoxides; esters; ketones; aldehydes; and nitriles. Illustrative of suitable optically active and non-optically active compounds which can be prepared by the processes of this invention (including starting material compounds as described hereinabove) include those permissible compounds which are described in Kirk-Othmer, Encyclopedia of Chemical Technology, Fourth Edition, 1996, the pertinent portions of which are incorporated herein by reference, and The Merck Index, An Encyclopedia of Chemicals, Drugs and Biologicals, Eleventh Edition, 1989, the pertinent portions of which are incorporated herein by reference.

In accordance with one embodiment of this invention, one or more reactants are reacted in the presence of a metal-organophosphorus ligand complex catalyst, optionally free organophosphorus ligand, a polar solvent and a nonpolar solvent to form a multiphase reaction product fluid and this fluid is then separated to obtain one phase comprising the one or more reactants, metal-organophosphorus ligand complex catalyst, optionally free organophosphorus ligand and polar solvent and at least one other phase comprising one or more products and nonpolar solvent. During the reaction, the reaction product fluid comprising one or more reactants, a metal-organophosphorus ligand complex catalyst, optionally free organophosphorus ligand, one or more products and a polar solvent is in intimate contact with the nonpolar solvent such that the one or more products are extracted selectively into the nonpolar solvent. This extraction is followed by phase separation in which a layer of the extraction fluid, i.e., nonpolar solvent and one or more products, is separated from a layer of the reaction product fluid.

In accordance with another embodiment of this invention, one or more reactants are reacted in the presence of a metal-organophosphorus ligand complex catalyst, optionally free organophosphorus ligand and a polar solvent to form a reaction product fluid, the reaction product fluid is then contacted with a nonpolar solvent to form a multiphase reaction product fluid, and this fluid is then separated to obtain one phase comprising the one or more reactants, metal-organophosphorus ligand complex catalyst, optionally free organophosphorus ligand and polar solvent and at least one other phase comprising the one or more products and nonpolar solvent. After the reaction, the reaction product fluid comprising one or more reactants, a metal-organophosphorus ligand complex catalyst, optionally free organophosphorus ligand, one or more products and a polar solvent is intimately contacted with the nonpolar solvent such that the one or more products are extracted selectively into the nonpolar solvent. This extraction is followed by phase separation in which a layer of the extraction fluid, i.e., nonpolar solvent and one or more products, is separated from a layer of the reaction product fluid.

As indicated above, the processes of this invention are conducted in the presence of a polar solvent and a nonpolar solvent, or in the presence of a polar solvent followed by mixing with a nonpolar solvent. The polar solvent may contain up to about 8 weight percent water, preferably less than about 6 weight percent water, and most preferably less than about 4 weight percent water. The presence of a small amount of water may improve extraction efficiency and provide stabilization of certain products. A large amount of water is undesirable because it may lead to the formation of multiphases, hydrolysis of certain phosphorous containing ligands, and decreased solubility of the ligand and/or catalyst in the polar solvent. It is to be understood that the processes of this invention are considered to be essentially "non-aqueous" processes, which is to say, any water present in the reaction mediums is not present in an amount sufficient to cause either the particular reaction or said medium to be considered as encompassing a separate aqueous or water phase or layer in addition to the organic phases. Depending on the particular catalyst and reactants employed, suitable polar solvents include, for example, nitriles, lactones, pyrrolidones, formamides, sulfoxides and the like. Examples of unsuitable polar solvents include simple alcohols, diols, triols, polyols, primary amines, secondary amines, and the like, since they can react with aldehyde products to give undesirable by-products which lead to lower reaction efficiencies and could complicate phase separations.

Mixtures of one or more different polar solvents may be employed if desired. The Hildebrand solubility parameter for the polar solvent or mixtures of one or more different polar solvents should be less than about 13.5 $(cal/cm^3)^{1/2}$ or 873 $(kJ/m^3)^{1/2}$, preferably less than about 13.0 $(cal/cm^3)^{1/2}$ or 841 $(kJ/m^3)^{1/2}$, and more preferably less than about 12.5 $(cal/cm^3)^{1/2}$ or 809 $(kJ/m^3)^{1/2}$. The amount of polar solvent employed is not critical to the subject invention and need only be that amount sufficient to provide the reaction medium with the particular metal concentration desired for a given process. In general, the amount of polar solvent employed may range from above at 5 percent by weight up to about 99 percent by weight or more based on the total weight of the reaction mixture.

Illustrative polar solvents useful in this invention include, for example, propionitrile, 1,3-dioxolane, 3-methoxypropionitrile, N-methylpyrrolidone, N,N-dimethylformamide, 2-methyl-2-oxazoline, adiponitrile, acetonitrile, epsilon caprolactone, glutaronitrile, 3-methyl-2-oxazolidinone, dimethyl sulfoxide and sulfolane. The solubility parameters of illustrative polar solvents are given in the Table below.

TABLE

Solubility Parameters of Illustrative Polar Solvents

| Polar Solvent | $\delta_{Solvent}$ $(cal/cm^3)^{1/2}$ | $\delta_{Solvent}$ $(kJ/m^3)^{1/2}$ |
|---|---|---|
| Propionitrile | 10.73 | 694 |
| 1,3-Dioxolane | 11.33 | 733 |
| 3-Methoxypropionitrile | 11.37 | 735 |
| N-Methylpyrrolidone | 11.57 | 748 |
| N,N-Dimethylformamide | 11.76 | 761 |
| 2-Methyl-2-Oxazoline | 12.00 | 776 |
| Adiponitrile | 12.05 | 779 |
| Acetonitrile | 12.21 | 790 |
| E-Caprolactone | 12.66 | 819 |
| Sulfolane | 12.80 | 828 |
| Glutaronitrile | 13.10 | 847 |
| Dimethyl Sulfoxide | 13.10 | 847 |
| 3-Methyl-2-Oxazolidinone | 13.33 | 862 |

The desired products of this invention can be selectively recovered by extraction and phase separation in a nonpolar solvent. As indicated above, the nonpolar solvent can be present with the polar solvent during the reaction or the reaction product fluid can be contacted with a nonpolar solvent after the reaction. The desired reaction product is preferably extracted from the reaction product fluid through the use of an appropriate nonpolar solvent such that any extraction of the one or more reactants, metal-organophosphorus ligand complex catalyst, and optionally free organophosphorus ligand from the reaction product fluid is minimized or eliminated. Depending on the particular desired products, suitable nonpolar solvents include, for example, alkanes, cycloalkanes, alkenes, aldehydes, ketones, ethers, esters, amines, aromatics, silanes, silicones, carbon dioxide, and the like. Examples of unsuitable nonpolar solvents include fluorocarbons and fluorinated hydrocarbons. These are undesirable due to their high cost, risk of environmental pollution, and the potential of forming multiphases.

Mixtures of one or more different nonpolar solvents may be employed if desired. The amount of nonpolar solvent employed is not critical to the subject invention and need only be that amount sufficient to extract the one or more products from the reaction product fluid for any given process. In general, the amount of nonpolar solvent employed may range from about 5 percent by weight up to about 50 percent by weight or more based on the total weight of the reaction product fluid.

Illustrative nonpolar solvents useful in this invention include, for example, propane, 2,2-dimethylpropane, butane, 2,2-dimethylbutane, pentane, isopropyl ether, hexane, triethylamine, heptane, octane, nonane, decane, isobutyl isobutyrate, tributylamine, undecane, 2,2,4-trimethylpentyl acetate, isobutyl heptyl ketone, diisobutyl ketone, cyclopentane, cyclohexane, isobutylbenzene, n-nonylbenzene, n-octylbenzene, n-butylbenzene, p-xylene, ethylbenzene, 1,3,5-trimethylbenzene, m-xylene, toluene, o-xylene, decene, docenene, tetradecene, and heptadecanal. The solubility parameters of illustrative nonpolar solvents are given in the Table below.

TABLE

Solubility Parameters of Illustrative Non-Polar Solvents

| Non-Polar Solvent | $\delta_{Solvent}$ $(cal/cm^3)^{1/2}$ | $\delta_{Solvent}$ $(kJ/m^3)^{1/2}$ |
|---|---|---|
| Propane | 5.76 | 373 |
| 2,2-Dimethylpropane | 6.10 | 395 |
| Butane | 6.58 | 426 |
| 2,2-Dimethylbutane | 6.69 | 433 |
| Pentane | 7.02 | 454 |
| Isopropyl Ether | 7.06 | 457 |
| Hexane | 7.27 | 470 |
| Triethylamine | 7.42 | 480 |
| Heptane | 7.50 | 485 |
| Octane | 7.54 | 488 |
| Nonane | 7.64 | 494 |
| Decane | 7.72 | 499 |
| Isobutyl Isobutyrate | 7.74 | 501 |
| Tributylamine | 7.76 | 502 |
| Undecane | 7.80 | 505 |
| 2,2,4-Trimethylpentyl Acetate | 7.93 | 513 |
| Isobutyl Heptyl Ketone | 7.95 | 514 |
| Diisobutyl Ketone | 8.06 | 521 |
| Cyclopentane | 8.08 | 523 |
| Cyclohexane | 8.19 | 530 |
| n-Nonylbenzene | 8.49 | 549 |
| n-Octylbenzene | 8.56 | 554 |
| n-Butylbenzene | 8.57 | 554 |
| p-Xylene | 8.83 | 571 |
| Ethylbenzene | 8.84 | 572 |

TABLE-continued

Solubility Parameters of Illustrative Non-Polar Solvents

| Non-Polar Solvent | $\delta_{Solvent}$ $(cal/cm^3)^{1/2}$ | $\delta_{Solvent}$ $(kJ/m^3)^{1/2}$ |
|---|---|---|
| 1,3,5-Trimethylbenzene | 8.84 | 572 |
| m-Xylene | 8.88 | 574 |
| Toluene | 8.93 | 578 |
| o-Xylene | 9.06 | 586 |

Extraction to obtain one phase comprising the one or more reactants, metal-organophosphorus ligand complex catalyst, optionally free organophosphorus ligand and polar solvent and at least one other phase comprising one or more products and nonpolar solvent is an equilibrium process. The relative volumes of the nonpolar solvent (or extraction solution) and the polar solvent or reaction product fluid in this extraction operation are determined in part by the solubility of the one or more reactants, metal-organophosphorus ligand complex catalyst, optionally free organophosphorus ligand and one or more products in the solvents used, and the amount of desired product to be extracted. For example, when the desired product is extracted, if the desired product to be extracted shows high solubility in the nonpolar solvent and is present at a relatively low concentration in the reaction product fluid, it is possible to extract the desired product by using the nonpolar solvent in a relatively small volume ratio to the reaction product fluid.

Further, as the concentration of the desired product becomes high, it is usually required to increase the ratio of the nonpolar solvent to the reaction product fluid for extracting the desired product from the reaction product fluid. When the desired product shows relatively low solubility in the nonpolar solvent, the relative volume of the nonpolar solvent or extraction solution will have to be increased. Generally, the volume ratio of the nonpolar solvent or extraction solution to the reaction product fluid may be changed within a range of from about 10:1 to about 1:10.

With respect to the extraction temperature, there is no merit in employing a temperature higher than the reaction temperature of the particular process, and desirable results can be obtained by employing an extraction temperature lower than the process reaction temperature. Depending on the particular process, extraction temperatures may range from about −80° C. or less to about 200° C. or greater.

The time for mixing the reaction product fluid with the nonpolar solvent, i.e. the time before the phase separation, depends on the rate until the two-phases reach the equilibrium condition. Generally, such a time maybe varied from within one minute or less to a long period of one hour or more.

The extraction process of this invention is in part an equilibrium process of an organophosphorus ligand dissolved in two separate liquid phases. The efficiency of this extraction process can be measured by a partition coefficient Kp of the organophosphorus ligand which is defined as follows:

$$Kp = \frac{\text{Concentration of organophosphorus ligand in the polar solvent after extraction}}{\text{Concentration of organophosphorus ligand in the nonpolar solvent after extraction}}$$

When the one or more desired products are partitioned between the reaction product fluid and the nonpolar solvent by the extraction process of this invention, the Kp value of the organophosphorus ligand can be maintained at a level greater than about 10, preferably greater than about 15, and more preferably greater than about 20, depending on the efficiency of the extraction process. If this Kp value is high, the extraction efficiency, will be high.

The extraction process of this invention is also in part an equilibrium process of one or more products dissolved in two separate liquid phases. The efficiency of this extraction process can be measured by a partition coefficient Kp of the one or more products which is defined as follows:

$$Kp = \frac{\text{Concentration of products in the nonpolar solvent after extraction}}{\text{Concentration of products in the polar solvent after extraction}}$$

When the one or more desired products are partitioned between the reaction product fluid and the nonpolar solvent by the extraction process of this invention, the Kp value of the products can be maintained at a level greater than about 0.5, preferably greater than about 0.75, and more preferably greater than about 1, depending on the efficiency of the extraction process. If this Kp value is high, the extraction efficiency will be high.

The extraction process of this invention may be conducted in one or more stages. The exact number of extraction stages will be governed by the best compromise between capital costs and achieving high extraction efficiency and ease of operability, as well as the stability of the starting materials and the desired reaction product to the extraction conditions. Also, the extraction process of this invention may be conducted in a batch or continuous fashion. When conducted continuously, the extraction may be conducted in a current or countercurrent manner or fractional extraction may be used.

Illustrative types of extractors that may be employed in this invention include, for example, columns, centrifuges, mixer-settlers, and miscellaneous devices. A description of these devices can be found in the Handbook of Solvent Extraction, ISBN 0-89464-546-3, Krieger Publishing Company, 1991, the disclosure of which is incorporated herein by reference. As used in this invention, the various types of extractors may be combined in any combination to effect the desired extraction.

Following the extraction, the desired products of this invention may be recovered by phase separation in which a layer of the extraction fluid, i.e., nonpolar solvent and one or more products, is separated from a layer of the reaction product fluid. The phase separation techniques may correspond to those techniques heretofore employed in conventional processes.

From a free energy standpoint, to attain dissolution or miscibility of a phosphorous containing ligand in a particular solvent, the enthalpy of mixing should be as small as possible. The enthalpy of mixing ($\Delta H_m$) can be approximated by the Hildebrand equation (1)

$$\Delta H_m = \Phi_S \Phi_L V(\delta_{Solvent} - \delta_{Ligand})^2 \quad (1)$$

using the solubility parameters of the solvent ($\delta_{Solvent}$) and ligand ($\delta_{Ligand}$), where V is the molar volume of the mixture, and $\Phi_S$ and $\Phi_L$ are the volume fractions of the solvent and ligand, respectively. Based on equation (1), the ideal solvent for a ligand would have the same solubility parameter as the ligand itself, so that $\Delta H_m = 0$. However, for each ligand there is a characteristic range originating from its solubility parameter which encloses all liquids that are solvents for the ligand. In general, a solvent or a solvent blend having a solubility parameter that is within two units of the solubility parameter of the ligand will dissolve the ligand; however, relatively large deviations from this value can sometimes occur, especially if there are strong hydrogen bonding interactions. Therefore, equation (2)

$$\delta_{solvent} - \delta_{Ligand} < 2.0 (\text{cal/cm}^3)^{1/2} \quad (2)$$

can be used semi-quantitatively to determine whether a liquid is a good Solvent for a given ligand. In equation (2), $\delta_{Solvent}$ and $\delta_{Ligand}$ represent the solubility parameters of the solvent and ligand respectively.

For purposes of this invention, the solubility parameters for solvents can be calculated from equation (3)

$$\delta_{solvent} = (\Delta H_v - RT)d/MW \quad (3)$$

in which $\Delta H_v$ is the heat of vaporization, R is a gas constant, T is temperature in degrees absolute, d is the density of the solvent, and MW is molecular weight of the solvent. The solubility parameters for a wide variety of solvents have been reported by K. L. Hoy, "New Values of the Solubility Parameters from Vapor Pressure Data," Journal of Paint Technology, 42, (1970), 76.

The heat of vaporization for phosphorous containing compounds cannot be easily measured since many of these compounds decompose at higher temperatures. Furthermore, since many phosphorous containing compounds are solids at room temperature, measurements of density are not convenient. The solubility parameters, in units of $(\text{cal/cm}^3)^{1/2}$, for phosphorus containing ligands can be calculated using equation (4)

$$\delta_{Ligand} = (\Sigma F_T + 135.1)/(0.01211 + \Sigma N_i V_{1i}) 1000 \quad (4)$$

from group contribution theory as developed by (1) K. L. Hoy, "New Values of the Solubility Parameters from Vapor Pressure Data," Journal of Paint Technology, 42, (1970), 76, and (2) L. Constantinou, R. Gani, J. P. O'Connell, "Estimation of the Acentric Factor and the Liquid Molar Volume at 298 K Using a New Group Contribution Method," Fluid Phase Equilibria, 103, (1995), 11. In equation (4), $\Sigma F_T$ is the sum of all the group molar attraction constants, and $\Sigma N_i V_{1i}$ is the sum of all the first order liquid molar volume constants $V_{1i}$, which occur $N_i$ times. These methods have been expanded to include the group molar attraction constant of 79.4 $(\text{cal/cm}^3)^{1/2}$ and first order liquid molar volume constant of 0.0124 m³/kmol for (>P–) derived from triphenylphosphine data found in T. E. Daubret, R. P. Danner, H. M. Sibul, and C. C. Stebbins, "DIPPR Data Compilation of Pure Compound Properties," Project 801, Sponsor Release, July 1995, Design Institute for Physical Property Data, AIChE, A New York, N.Y.

The processes of this invention can be conducted in a batch or continuous fashion, with recycle of unconsumed starting materials if required. The reaction can be conducted in a plurality of reaction zones, in series or in parallel or it may be conducted batchwise or continuously in an elongated tubular zone or series of such zones. For example, a backmixed reactor may be employed in series with a multistaged reactor with the backmixed reactor being first. The materials of construction employed should be inert to the starting materials during the reaction and the fabrication of the equipment should be able to withstand the reaction temperatures and pressures. Means to introduce and/or adjust the quantity of starting materials or ingredients introduced batchwise or continuously into the reaction zone during the course of the reaction can be conveniently utilized in the processes especially to maintain the desired molar ratio of the starting materials. The reaction steps may be effected by the incremental addition of one of the starting materials to the other. Also, the reaction steps can be combined by the joint addition of the starting materials. When complete conversion is not desired or not obtainable, the starting materials can be separated from the product, and the starting materials then recycled back into the redaction zone.

The processes may be conducted in either glass lined, stainless steel or similar type reaction equipment. The reaction zone may be fitted with one or more internal and/or external heat exchanger(s) in order to control undue temperature fluctuations, or to prevent any possible "runaway" reaction temperatures.

The processes of this invention may be Conducted in one or more reaction steps and more than one reactive stages. The exact number of reaction steps and reactive stages will be governed by the best compromise between capital costs and achieving high catalyst selectivity, activity, lifetime and ease of operability, as well as the intrinsic reactivity of the starting materials in question and the stability of the starting materials and the desired reaction product to the reaction conditions.

Hydroformylation Processes

A preferred process useful in this invention is hydroformylation. Illustrative metal-organophosphoris ligand complex catalyzed hydroformylation processes as described, for example, in U.S. Pat. Nos. 4,148,830; 4,593, 127; 4,769,498; 4,717,775; 4,774,361; 4,885,401; 5,264, 616; 5,288,918; 5,360,938; 5,364,950; and 5,491,266; the disclosures of which are incorporated herein by reference. Accordingly, the hydroformylation processing techniques of this invention may correspond to any known processing techniques. Preferred process are those involving catalyst liquid recycle hydroformylation processes.

In general, such catalyst liquid recycle hydroformylation processes involve the production of aldehydes by reacting an olefinic unsaturated compound with carbon monoxide and hydrogen in the presence of a metal-organ phosphorus ligand complex catalyst in a liquid medium that also contains a solvent for the catalyst and ligand. Preferably free organophosphorus ligand is also present in the liquid hydroformylation reaction medium. The recycle procedure generally involves withdrawing a portion of the liquid reaction medium containing the catalyst and aldehyde product from the hydroformylation reactor (i.e., reaction zone), either continuously or intermittently, and recovering the aldehyde product therefrom in accordance with the separation techniques of this invention.

In a preferred embodiment, the hydroformylation reaction mixtures employable herein includes any mixture derived from any corresponding hydroformylation process that contains at least some amount of four different main ingredients or components, i.e., the aldehyde product, a metal-organophosphorus ligand (complex catalyst, free organophosphorus ligand and an organic solubilizing agent, e.g., polar solvent, for said catalyst and said free ligand, said ingredients corresponding to those employed and/or produced by the hydroformylation process from whence the hydroformylation reaction mixture starting material may be derived. It is to be understood that the hydroformylation reaction mixture compositions employable herein can and normally will contain minor amounts of additional ingredients such as those which have either been deliberately employed in the hydroformylation process or formed in situ during said process. Examples of such ingredients that can also be present include unreacted olefin starting material, carbon monoxide and hydrogen gases, and in situ formed type products, such as saturated hydrocarbons and/or unreacted isomerized olefins corresponding to the olefin starting materials, and high boiling liquid aldehyde condensation byproducts, as well as other inert co-solvent, e.g., nonpolar solvent, type materials or hydrocarbon additives, if employed.

The substituted or unsubstituted olefin reactants that may be employed in the hydroformylation processes (and other suitable processes) of this invention include both optically active (prochiral and chiral) and non-optically active (achiral) olefinic unsaturated compounds containing from 2 to 40, preferably 2 to 20, carbon atoms. Such olefinic unsaturated compounds can be terminally or internally unsaturated and be of straight-chain, branched chain or cyclic structures, as well as olefin mixtures, such as obtained from the oligomerization of propene, butene, isobutene, etc. (such as so called dimeric, trimeric or tetrameric propylene and the like, as disclosed, for example, in U.S. Pat. Nos. 4,518,809 and 4,528,433). Moreover, such olefin compounds may further contain one or more ethylenic unsaturated groups, and of course, mixtures of two or more different olefinic unsaturated compounds may be employed as the starting material if desired. For example, commercial alpha olefins containing four or more carbon atoms may contain minor amounts of corresponding internal olefins and/or their corresponding saturated hydrocarbon and that such commercial olefins need not necessarily be purified from same prior to being reacted. Illustrative mixtures of olefinic starting materials that can be employed in the hydroformylation reactions include, for example, mixed butenes, e.g., Raffinate I and II. Further such olefinic unsaturated compounds and the corresponding products derived therefrom may also contain one or more groups or substituents which do not unduly adversely affect the processes of this invention such as described, for example, in U.S. Pat. Nos. 3,527,809, 4,769,498 and the like.

Most preferably the subject invention is especially useful for the production of non-optically active aldehydes, by hydroformylating achiral alpha-olefins containing from. 2 to 30, preferably 2 to 20, carbon atoms, and achiral internal olefins containing from 2 to 20 carbon atoms as well as starting material mixtures of such alpha olefins and internal olefins.

Illustrative alpha and internal olefins include, for example, ethylene, propylene, 1-butene, 1-pentene, 1-hexene, 1-octene, 1-nonene, 1-decene, 1-undecene, 1-dodecene, 1-tridecene, 1-tetradecene, 1-pentadecene, 1-hexadecene, 1-heptadecene, 1-octadecene, 1-nonadecene, 1-eicosene, 2-butene, 2-methyl propene (isobutylene), 2-methylbutene, 2-pentene, 2-hexene, 3-hexane, 2-heptene, 2-octene, cyclohexane, propylene dimers, propylene trimers, propylene tetramers, butadiene, piperylene, isoprene, 2-ethyl-1-hexene, styrene, 4-methyl styrene, 4-isopropyl styrene, 4-tert-butyl styrene, alpha-methyl styrene, 4-tert-butyl-alpha-methyl styrene, 1,3-diisopropenylbenzene, 3-phenyl-1-propene, 1,4-hexadiene, 1,7-octadiene, 3-cyclohexyl-1-butene, and the like, as well as, 1,3-dienes, butadiene, pentenoic acids and salts, e.g., salts of 3- and 4-pentenoic acids, alkyl alkenoates, e.g., methyl pentenoate, alkenyl alkanoates, alkenyl alkyl ethers, alkenols, e.g., pentenols, alkenals, e.g., pentenals, and the like, such as allyl alcohol, allyl butyrate, hex-1-en-4-ol, oct-1-en-4-ol, vinyl acetate, allyl acetate, 3-butenyl acetate, vinyl propionate, allyl propionate, methyl methacrylate, vinyl ethyl ether, vinyl methyl ether, allyl ethyl ether, n-propyl-7-octenoate, 3-butenenitrile, 5-hexenamide, eugenol, iso-eugenol, safrole, iso-safrole, 4-allylanisole, indene, limonene, beta-pinene, dicyclopentadiene, cyclooctadiene, camphene, linalool, and the like.

Illustrative prochiral and chiral olefins useful in the asymmetric hydroformylation processes (and other asymmetric processes) that can be employed to produce enantiomeric product mixtures that may be encompassed by in this invention include those represented by the formula:

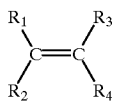

(XIII)

wherein $R_1$, $R_2$, $R_3$ and $R_4$ are the same or different (provided $R_1$ is different from $R_2$ or $R_3$ is different from $R_4$) and are selected from hydrogen; alkyl; substituted alkyl, said substitution being selected from dialkylamino such as benzylamino and dibenzylamino, alkoxy such as methoxy and ethoxy, acyloxy such as acetoxy, halo, nitro, nitrile, thio, carbonyl, carboxamide, carboxaldehyde, caroboxyl, carboxylic ester; aryl including phenyl; substituted aryl including phenyl, said substitution being selected from alkyl, amino including alkylamino and dialkylamino such as benzylamino and dibenzylamino, hydroxy, alkoxy such as methoxy and ethoxy, acyloxy such as acetoxy, halo, nitrile, nitro, carboxyl, carboxaldehyde, carboxylic ester, carbonyl, and thio; acyloxy such as acetoxy; alkoxy such as methoxy and ethoxy; amino including alkylamino and dialkylamino such as benzylamino and dibenzylamino; acylamino and diacylamino such as acetylbenzylamino and diacetylamino; nitro; carbonyl; nitrile; carboxyl; carboxamide; carboxaldehyde; carboxylic ester; and alkylmercapto such as methylmercapto. It is understood that the prochiral and chiral olefins of this definition also include molecules of the above general formula where the R groups are connected to form ring compounds, e.g., 3-methyl-1-cyclohexane, and the like.

Illustrative optically active or prochiral olefinic compounds useful in asymmetric hydroformylation processes (and other asymmetric processes) of this invention include, for example, p-isobutylstyrene, 2-vinyl-6-methoxy-2-naphthylene, 3-ethenylphenyl phenyl ketone, 4-ethenylphenyl-2-thienylketone, 4-ethenyl-2-fluorobiphenyl, 4-(1,3-dihydro-1-oxo-2H-isoindol-2-yl) styrene, 2-ethenyl-5-benzoylthiophene, 3-ethenylphenyl phenyl ether, propenylbenzene, isobutyl-4-propenylbenzene, phenyl vinyl ether and the like. Other olefinic compounds include substituted aryl ethylenes as described, for example, in U.S. Pat. Nos. 4,329,507, 5,360,938 and 5,491,266, the disclosures of which are incorporated herein by reference.

Illustrative of suitable substituted and unsubstituted olefinic starting materials include those permissible substituted and unsubstituted olefinic compounds described in Kirk-Othmer, Encyclopedia of Chemical Technology, Fourth Edition, 1996, the pertinent portions of which are incorporated herein by reference.

As noted, the hydroformylation processes of this invention involve the use of a metal-organophosphorus ligand complex catalyst as described hereinabove. Of course mixtures of such catalysts can also be employed if desired. The amount of metal-organophosphorus ligand complex catalyst present in the reaction medium of a given hydroformylation process encompassed by this invention need only be that minimum amount necessary to provide the given metal concentration desired to be employed and which will furnish the basis for at least the catalytic amount of metal necessary to catalyze the particular hydroformylation process involved such as disclosed, for example, in the above-mentioned patents. In general, metal, e.g., rhodium, concentrations in the range of from about 10 parts per million to about 1000 parts per million, calculated as free rhodium, in the hydroformylation reaction medium should be sufficient for most processes, while it is generally preferred to employ from about 10 to 500 parts per million of metal, e.g., rhodium, and more preferably from 25 to 400 parts per million of metal, e.g., rhodium.

In addition to the metal-organophosphorus ligand complex catalyst, free organophosphorus ligand (i.e., ligand that is not complexed with the metal) may also be present in the hydroformylation reaction medium. The free organophosphorus ligand may correspond to any of the above-defined organophosphorus ligands (employable herein. It is preferred that the free organophosphorus ligand be the same as the organophosphorus ligand of the metal-organophosphorus ligand complex catalyst employed. However, such ligands need not be the same in any given process. The hydroformylation process of this invention may involve from about 0.1 moles or less to about 400 moles or higher, of free organophosphorus ligand per mole of metal in the hydroformylation reaction medium. Preferably the hydroformylation process of this invention is carried out in the presence of from about 1 to about 200 moles of organophosphorus ligand, and more preferably for organopolyphosphites from about 1.1 to about 4 moles of organopolyphosphite ligand, per mole of metal present in the reaction medium; said amounts of organophosphorus ligand being the sum of both the amount of organophosphorus ligand that is bound (complexed) to the metal present and the amount of free (non-complexed) organophosphorus ligand present. Since it is more preferred to produce non-optically active aldehydes by hydroformylating achiral olefins, the more preferred organophosphorus ligands are achiral type organophosphorus ligands, especially those encompassed by Formula (I) above, and more preferably those of Formulas (II) and (V) above. Of course, if desired, make-up or additional organophosphorus ligand can be supplied to the reaction medium of the hydroformylation process at any time and in any suitable manner, e.g. to maintain a predetermined level of free ligand in the reaction medium.

The reaction conditions of the hydroformylation processes encompassed by this invention may include any suitable type hydroformylation conditions heretofore employed for producing optically active and/or non-optically active aldehydes. For instance, the total gas pressure of hydrogen, carbon monoxide and olefin starting compound of the hydroformylation process may range from about 1 to about 10,000 psia. In general, however, it is preferred that the process be operated at a total gas pressure of hydrogen, carbon monoxide and olefin starting compound of less than about 2000 psia and more preferably less than about 1000 psia. The minimum total pressure is limited predominately by the amount of reactants necessary to obtain a desired rate of reaction. More specifically the carbon monoxide partial pressure of the hydroformylation process of this inventions is preferable from about 1 to about 1000 psia, and more preferably from about 3 to about 800 psia, while the hydrogen partial pressure is preferably about 5 to about 500 psia and more preferably from about 10 to about 300 psia. In general $H_2$:CO molar ratio of gaseous hydrogen to carbon monoxide may range from about 1:10 to 100:1 or higher, I-he more preferred hydrogen to carbon monoxide molar ratio being from about 1:10 to about 10:1. Further, the hydroformylation process, may be conducted at a reaction temperature from about −25° C. to about 200° C. In general hydroformylation reaction temperatures of about 50° C. to about 120° C. are preferred for all types of olefinic starting materials. Of course it is to be understood that when non-optically active aldehyde products are desired, achiral type olefin starting materials and organophosphorus ligands are employed and when optically active aldehyde products are desired prochiral or chiral type olefin starting materials and organophosphorus ligands are employed. Of course, it is to be also understood that the hydroformylation reaction conditions employed will be governed by the type of aldehyde product desired.

Accordingly illustrative non-optically active aldehyde products include e.g., propionaldehyde, n-butyraldehydle, isobutyraldehyde, n-valeraldehyde, 2-methyl 1-butyraldehyde, hexanal, hydroxyhexanal, 2-methyl valeraldehyde, helitanal, 2-methyl 1-hexanal, octanal, 2-methyl 1-heptanal, nonanal, 2-methyl-1-octanal, 2-ethyl 1-heptanal, 3-propyl 1-hexanal, decanal, adipaldehyde, 2-methylglutaraldehyde, 2-methyladipaldehyde, 3-methyladipaldehyde, 3-hydroxypropionaldehyde, 6-hydroxyhexanal, alkenals, e.g., 2-, 3- and 4-pentenal, formylvaleric acids and salts, e.g., salts of 5-formylvaleric acid, alkyl 5-formylvalerate, 2-methyl-1-nonanal, undecanal, 2-methyl 1-decanal, dodecanal, 2-methyl 1-undecanal, tridecanal, 2-methyl 1-tridecanal, 2-ethyl, 1-dodecanal, 3-propyl-1-undecanal, pentadecanal, 2-methyl-1-tetradecanal, hexadecanal, 2-methyl-1-pentadecanal, heptadecanal, 2-methyl-1-hexadecanal, octadecanal, 2-methyl-1-heptadecanal, nonodecanal, 2-methyl-1-octadecanal, 2-ethyl 1-heptadecanal, 3-propyl-1-hexadecanal, eicosanal, 2-methyl-1-nonadecanal, heneicosanal, 2-methyl-1-eicosanal, tricosanal, 2-methyl-1-docosanal, tetracosanal, 2-methyl-1-tricosanal, pentacosanal, 2-methyl-1-tetracosanal, 2-ethyl 1-tricosanal, 3-propyl-1-docosanal, heptacosanal, 2-methyl-1-octacosanal, nonacosanal, 2-methyl-1-octacosanal, hentriacontanal, 2-methyl-1-triacontanal, and the like.

Illustrative optically active aldehyde products include (enantiomeric) aldehyde compounds prepared by the asymmetric hydroformylation process of this invention such as, e.g. S-2-(p-isobutylphenyl)-propionaldehyde, S-2-(6-methoxy-2-naphthyl)propionaldehyde, S-2-(3-benzoylphenyl)-propionaldehyde, S-2-(p-thienoylphenyl) propionaldehyde, S-2-(3-fluoro-4-phenyl) phenylpropionaldehyde, S-2- [4-(1,3-dihydro- 1-oxo-2H-isoindol-2-yl)phenyl]propionaldehyde, S-2-(2-methylacetaldehyde)-5-benzoylthiophene and the like.

Illustrative of suitable substituted and unsubstituted aldehyde products include those permissible substituted and unsubstituted aldehyde compounds described in Kirk-Othmer, Encyclopedia of Chemical Technology, Fourth Edition, 1996, the pertinent portions of which are incorporated herein by reference.

In accordance with this invention, the aldehyde product mixtures may be extracted and separated from the other components of the crude reaction mixtures in which the aldehyde mixtures are produced by phase separation as described above.

It is generally preferred to carry out the hydroformylation processes of this invention in a continuous manner. In general, continuous hydroformylation processes are well known in the art and may involve: (a) hydroformylating the olefinic starting material(s) with carbon monoxide and hydrogen in a liquid homogeneous reaction mixture comprising a polar solvent, the metal-organophosphorus ligand complex catalyst, free organophosphorus ligand, and optionally a nonpolar solvent; (b) maintaining reaction temperature and pressure conditions favorable to the hydroformylation of the olefinic starting material(s); (c) supplying make-up quantities of the olefinic starting material(s), carbon monoxide and hydrogen to the reaction medium as those reactants are used up; (d) mixing at least a portion of the reaction medium with a nonpolar solvent to extract the desired aldehyde hydroformylation product(s) from the reaction medium; and (e) recovering the desired aldehyde product(s) by phas;e separation.

At the conclusion of (or during) the process of this invention, the desired aldehydes may be recovered from the reaction mixtures used in the process of this invention. For instance, in a continuous liquid catalyst recycle process the portion of the liquid reaction mixture (containing aldehyde product, catalyst, etc.) removed from the reaction zone can be passed to a separation zone wherein the desired aldehyde product can be extracted and separated via phase separation from the liquid reaction mixture, and further purified if desired. The remaining catalyst containing liquid reaction mixture may then be recycled back to the reaction zone as may if desired any other materials, e.g., unreacted olefin, together with ally hydrogen and carbon monoxide dissolved in the liquid reaction after separation thereof from the aldehyde product.

For purposes of this invention, the term "hydrocarbon" is contemplated to include all permissible compounds having at least one hydrogen and one carbon atom. Such permissible compounds may also have one or more heteroatoms. In a broad aspect, the permissible hydrocarbons include acyclic (with or without heteroatoms) and cyclic, branched and unbranched, carbocyclic and heterocyclic, aromatic and nonaromatic organic compounds which can be substituted or unsubstituted.

As used herein, the term "substituted" is contemplated to include all permissible substituents of organic compounds unless otherwise indicated. In a broad aspect, the permissible substituents include acyclic and cyclic, branched and unbranched, carbocyclic and heterocyclic, aromatic and nonaromatic substituents of organic compounds. Illustrative substituents include, for example, alkyl, alkyloxy, aryl, aryloxy, hydroxy, hydroxyalkyl, amino, aminoalkyl, halogen and the like in which the number of carbons can range from 1 to about 20 or more, preferably from 1 to about 12. The permissible substituents can be one or more and the same or different for appropriate organic compounds. This invention is not intended to be limited in any manner by the permissible substituents of organic compounds.

Certain of the following examples are provided to further illustrate this invention. It is to be understood that all manipulations were carried out under a nitrogen atmosphere unless otherwise stated. Also, all examples were carried out at ambient temperature unless otherwise stated.

The ligands set out below are used in the following examples.

Ligand A
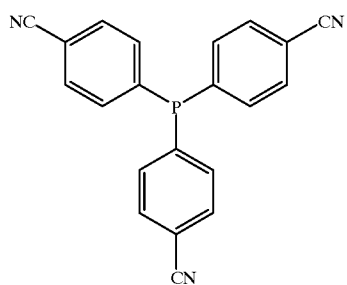
Ligand B
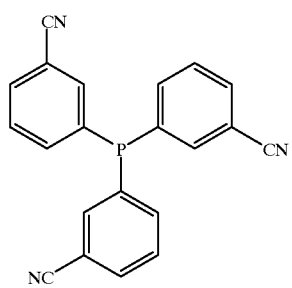
Ligand C
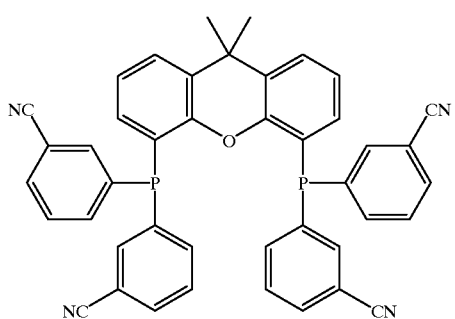
Ligand D
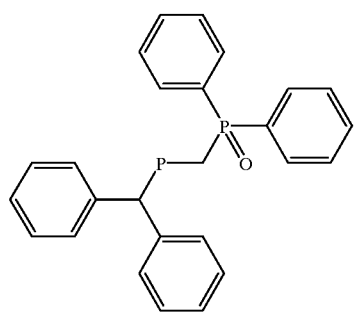
Ligand E
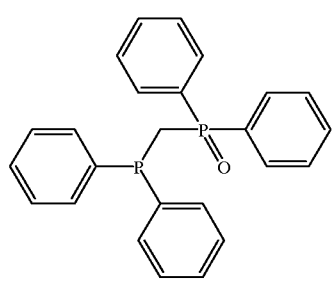
Ligand F
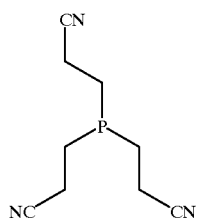
Ligand G
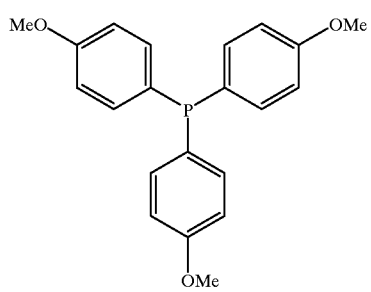
Ligand H
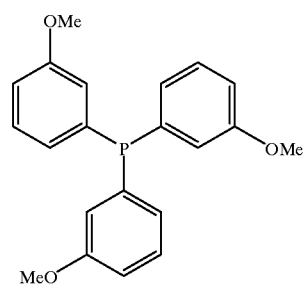
Ligand I
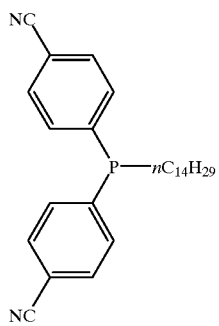
Ligand J
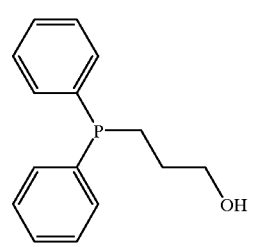

Ligand K

Ligand L

Ligand M

Ligand N

Ligand O

Ligand P

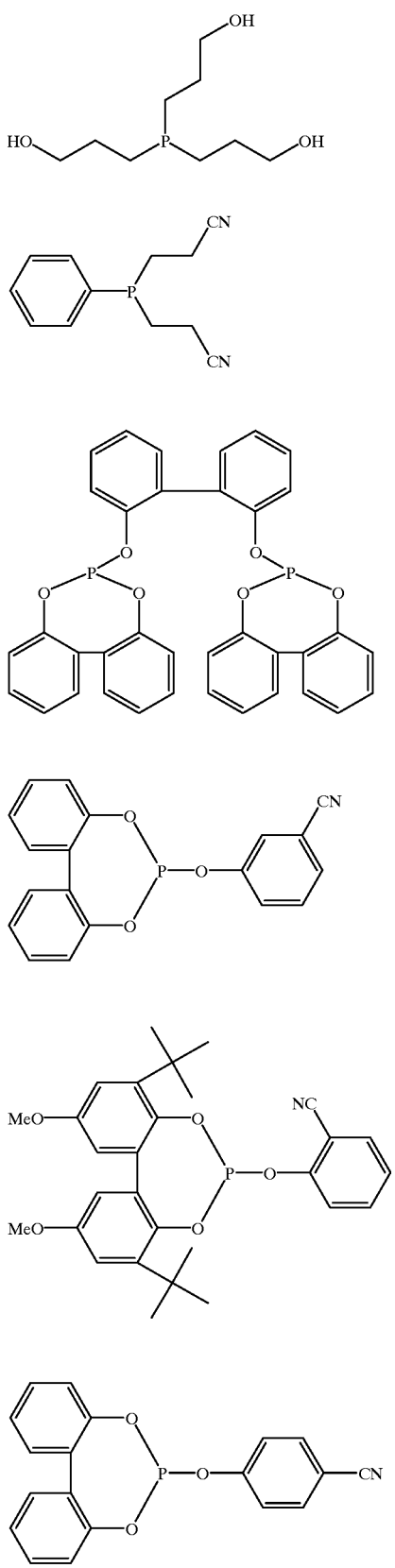

Ligand Q

Ligand R

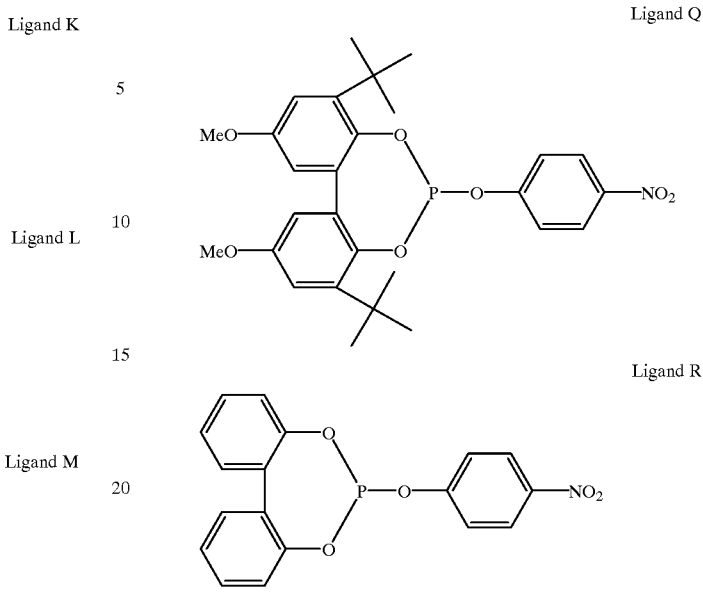

Solubility parameters and partition coefficients of illustrative ligands, certain of which are used in the examples below, are given in the following table.

TABLE

| Ligand | Solubility Parameter $(cal/cm^3)^{1/2}$ | Solubility Parameter $(kJ/m^3)^{1/2}$ | Kpartition* |
|---|---|---|---|
| Trioctylphosphine | 7.6 | 492 | <0.01 |
| Tricyclohexylphoshine | 8.1 | 524 | <0.2 |
| Cyclohexyldiphenylphosphine | 9.1 | 589 | 0.4 |
| Triphenylphosphine | 9.7 | 627 | 1.3 |
| Bis-(diphenylphosphino)ethane (DPPE) | 9.4 | 608 | 7.0 |
| A | 13.0 | 841 | 430 |
| B | 13.0 | 841 | 470 |
| D | 12.0 | 776 | 920 |
| E | 12.2 | 789 | 620 |
| F | 12.0 | 776 | >100 |
| G | 10.7 | 692 | 11 |
| I | 9.9 | 640 | 7 |
| J | 10.5 | 679 | 26 |
| K | 12.6 | 815 | >100 |
| L | 11.0 | 712 | >100 |
| M | 11.2 | 724 | 25 |
| N | 11.8 | 763 | 28 |
| O | 10.6 | 686 | 5.2 |
| P | 11.8 | 763 | 30 |
| Q | 10.5 | 679 | 5.3 |
| R | 11.6 | 750 | 22 |

*Partition coefficients based on examples with acetonitrile and hexane

Comparative Examples A–F

A stock solution of hexane containing approximately 2.5 percent by weight of triphenylphosphine (TPP) was prepared. A 5.0 milliliter aliquot was then added to a small vial containing 5.0 milliliter of a polar solvent identified in Table A. The mixture was shaken vigorously and then was allowed to phase separate. The two layers were analyzed for ligand content by gas chromatography (GC). Table A indicates the partition coefficient, which was determined by the ratio of the GC area for TPP in the polar phase to the nonpolar phase. Comparative Example 6 was analyzed via high performance liquid chromatography (HPLC) using a reverse phase column.

Comparative Examples G–K

A stock solution was prepared of hexane containing approximately 2.5 percent by weight of cyclohexyldiphenylphosphine (CHDPP). A 5.0 milliliter aliquot was then added to a small vial containing 5 milliliters of a polar solvent indicated in Table A. The mixture was shaken vigorously and then allowed to phase separate. The two layers were analyzed for ligand content by GC. Table A indicates the partition coefficient, which was determined by the ratio of the GC area for CHDPP in the polar phase to the hexane phase.

Comparative Example L

A 1 milliliter aliquot of a hexane solution containing approximately 0.1 percent by weight of tri-n-octylphosphine (TOP) was added to a small vial. To this vial was then added a 1 milliliter aliquot of acetonitrile. The mixture was vigorously shaker, and then allowed to phase separate. The two layers were then separated and each layer analyzed for ligand content by $^{31}$P NMR.

Comparative Example M

A 1 milliliter aliquot of a hexane solution containing approximately 0.1 percent by weight of tricyclohexylphosphine (TCHP) was added to a small vial. To this vial was then added a 1 milliliter aliquot of acetonitrile. The mixture was vigorously shaken and then allowed to phase separate. The two layers were then separated and each layer analyzed for ligand content by $^{31}$P NMP.

EXAMPLE 1

A solution was prepared containing approximately 0.1 percent by weight of Ligand A in 5.0 milliliters of acetonitrile. To this solution was added 5 milliliters of hexane. The mixture was then shaken vigorously and then allowed to phase separate. The two layers were analyzed for ligand content by HPLC. Table A indicates the partition coefficient, which was determined by the ratio of the HPLC area for Ligand A in the polar phase to the hexane phase.

EXAMPLES 2–6

The procedure in Example 1 was repeated with the modification of using dimethyl sulfoxide (Example 2), dimethyl formamide (Example 3), 3-methyl-2-oxazolidinone (Example 4), adiponitrile (Example 5), and ε-caprolactone (Example 6) as the polar solvents in place of acetonitrile. Table A indicates the measured Kpartition for Ligand A for the polar solvent/hexane solvent mixtures.

EXAMPLES 7–10

The procedure in Example 1 was repeated with the modification of using Ligand B in place of Ligand A. The polar solvents utilized were acetonitrile (Example 7) dimethyl sulfoxide (Example 8), dimethyl formamide (Example 9) and epsilon caprolactone (Example 10). Table A indicates the measured Kpartition for Ligand B for the polar solvent/hexane solvent mixtures.

TABLE A

| Example | Ligand (SP*) | Phases (SP*) | Kpartition |
|---|---|---|---|
| Comparative A | TPP (9.5) | Acetonitrile(12.21)/hexane(7.27) | 1.3 |
| Comparative B | TPP | DMSO(13.1)/hexane | 2.3 |
| Comparative C | TPP | DMF(11.76)/hexane | 5.9 |
| Comparative D | TPP | 3-methyl-2-oxazolidinone(13.33)/hexane | 4.3 |
| Comparative E | TPP | Adiponitrile(12.05)/hexane | 0.4 |
| Comparative F | TPP | Caprolactone/hexane | 3 |
| Comparative G | CHDPP (9) | Acetonitrile/hexane | 0.5 |
| Comparative H | CHDPP | DMSO/hexane | 0.5 |
| Comparative I | CHDPP | DMF/hexane | 2 |
| Comparative J | CHDPP | 3-methyl-2-oxazolidinone/hexane | 1.2 |
| Comparative K | CHDPP | Adiponitrile/hexane | 0.4 |
| Comparative L | TOP | Acetonitrile/hexane | <0.01** |
| Comparative M | TCHP | Acetonitrile/hexane | 0.2 |
| 1 | A (13) | Acetonitrile/hexane | 430 |
| 2 | A | DMSO/hexane | >1000 |
| 3 | A | DMF/hexane | >1000 |
| 4 | A | 3-methyl-2-oxazolidinone/hexane | >1000 |
| 5 | A | Adiponitrile/hexane | >1000 |
| 6 | A | Caprolactone/hexane | >1000 |
| 7 | B (13) | Acetonitrile/hexane | 470 |
| 8 | B | DMSO/hexane | 550 |
| 9 | B | DMF/hexane | 470 |
| 10 | B | Caprolactone/hexane | 960 |

*SP = solubility parameter
**-Kpartition determined using $^{31}$P NMR; the indicated ligand was not detected in the acetonitrile phase after extraction.

The above Examples show that phosphine ligands having high Hildebrand solubility parameters provide more favorable partition to the polar phase over the nonpolar phase.

EXAMPLES 11–13

The procedure in Example 1 was repeated with the modification of using Ligand D in place of Ligand A. The polar solvents utilized were acetonitrile (Example 11) dimethyl sulfoxide (Example 12), and dimethyl formamide (Example 13). Table B the measured Kpartition for Ligand D for the polar solvent/hexane solvent mixtures.

EXAMPLES 14–17

The procedure in Example 1 was repeated with the modification of using Ligand E in place of Ligand A. The polar solvents examined were acetonitrile (Example 14) dimethyl sulfoxide (Example 15), dimethyl formamide (Example 16), and caprolactone (Example 17). Table B indicates the measured Kpartition for Ligand E for the polar solvent/hexane solvent mixtures.

Comparative Example N

A solution was prepared containing approximately 0.1 percent by weight of bis(diphenylphosphino)ethane (DPPE) in 2.0 milliliters of acetonitrile. To this solution was added 2 milliliters of hexane. The mixture was then shaken vigorously and then allowed to phase separate. The two layers were analyzed for ligand content by $^{31}$P NMR. Table B indicates the partition coefficient, which was determined by the ratio of the $^{31}$P NMR peak height for DPPE in the acetonitrile phase to the hexane phase.

TABLE B

| Example | Ligand (SP*) | Phases (SP*) | Kpartition |
|---|---|---|---|
| 11 | D (11) | Acetonitrile/hexane | 920 |
| 12 | D | DMSO/hexane | 440 |
| 13 | D | DMF/hexane | 60 |
| 14 | D | Caprolactone/hexane | 80 |
| 15 | E (11) | Acetonitrile/hexane | 80 |
| 16 | E | DMSO/hexane | 620 |
| 17 | E | DMF/hexane | 50 |
| Comparative N | DPPE | Acetonitrile/hexane | 7 |

*SP = solubility parameter

The above Examples show that introducing an oxide to one of the phosphines of a bisphosphine increases the partition coefficient of the ligand into the polar phase.

EXAMPLE 18

A solution was prepared containing approximately 0.5 percent by weight of Ligand F in 2.0 milliliters of acetonitrile. To this solution was added 2 milliliters of hexane. The mixture was then shaken vigorously and then allowed to phase separate. The two layers were analyzed for ligand content by $^{31}$P NMR. Table C indicates the partition coefficient, which was determined by the ratio of the $^{31}$P NMR peak height for Ligand G in the acetonitrile phase to the hexane phase.

EXAMPLES 19–23

The procedure described in Example 18 was repeated with the modification of using Ligands G, I, J, K, and L (0.5 to 1 percent by weight) in place Ligand F, and analyzing the separate layers by $^{31}$P NMR for ligand content. The results from the extraction experiments are summarized in Table C.

TABLE C

| Example | Ligand | Kpartition |
|---|---|---|
| 18 | F | >100 |
| 19 | G | 11 |
| 20 | I | 7 |
| 21 | J | 26 |
| 22 | K | >1000 |
| 23 | L | >100 |

EXAMPLE 24

A 1 milliliter aliquot of an acetonitrile solution containing approximately 0.1 percent by weight of Ligand M was added to a small vial. To this vial was then added a 1 milliliter aliquot of hexane. The mixture was vigorously shaken and then allowed to phase separate. The two layers were then separated and analyzed for ligand content by $^{31}$P NMR. Table D indicates the partition coefficient, which was determined by the ratio of the $^{31}$P NMR peak height for Ligand M in the polar phase to the hexane phase

EXAMPLES 25–29

The procedure described in Example 24 was repeated with the modification of using Ligands N, O, P, Q, and R in place of Ligand M, and analyzing the separate layers by HPLC for ligand content. In Table D which follows, the results from the extraction experiments are summarized.

TABLE D

| Example | Ligand | Kpartition |
|---|---|---|
| 24 | M | 25 |
| 25 | N | 28 |
| 26 | O | 5.2 |
| 27 | P | 30 |
| 28 | Q | 5.3 |
| 29 | R | 22 |

EXAMPLE 30

A catalyst solution was prepared with 8.7 milligrams of dicarbonylacetylacetonato rhodium (I) (355 ppm), and 0.569 grams of Ligand A, and 9.20 grams of DMF. The catalyst (10 milliliters, 9.4 grams) and 1-tetradecene (3.9 grams, 5.0 milliliters) was charged to a 100 milliliter autoclave under inert gas at ambient temperature. The autoclave was heated to 90° C. with a band heater, the pressure was adjusted to 20 psi with nitrogen, then 80 psi of 1:1 hydrogen:carbon monoxide (syn gas) was added. The reaction rate was measured via 5 psi pressure drops using syn gas as the makeup gas. Gas consumption was measure until no further gas uptake was observed. The discharged reaction mixture remained one phase at room temperature. GC analysis indicated nearly complete consumption of the α-olefin. Table E outlines the results from the hydroformylation. An equal amount by weight of hexanes was then added to the reaction solution to cause phase separation. After shaking then allowing the solution to phase separate, a highly colored bottom phase and a colorless top phase were observed. GC analysis determined the top layer to be the nonpolar phase and the bottom layer to be the polar phase. Since the rhodium complexes formed with the ligand are highly colored, visual inspection can determine the phase containing the majority of the rhodium. The phase separated material was allowed to stand undisturbed for 4 days, then amount of rhodium in both phases was determined analytically determined. Table E outlines the results from rhodium analysis and confirms that the color of the phases allows one to determine where the rhodium resides.

EXAMPLE 31

A catalyst solution was prepared with 9.9 milligrams of dicarbonylacetylacetonato rhodium (I) (339 ppm), and 0.647 grams of Ligand A, and 11.0 grams of DMSO. The catalyst (10 milliliters, 10.9 g) was charged to the autoclave, heated to 90° C., then 1-tetradecene (3.9 grams, 5.0 milliliters) was added via syringe. Hydroformylation was conducted as in Example 30. In this case, the discharged reaction mixture was two phases at ambient temperature. The bottom phase was highly colored, indicative of the catalyst, and the top phase was faintly colored. GC analysis both phases indicated that the top phase was the nonpolar product phase and the bottom phase was the polar catalyst phase. An equal amount of hexanes by weight was added to the catalyst discharge. The reaction was shaken vigorously then allowed to settle for 4 days. The rhodium content in both phases was determined analytically. The results from hydroformylation and rhodium analysis are summarized in Table E.

EXAMPLE 32

A catalyst solution was prepared with 10.1 milligrams of dicarbonylacetylacetonato rhodium (I) (329 ppm), and 0.661 grams of Ligand A, and 11.6 grams of 3-methyl-2- oxazolidinone. The catalyst (10 milliliters, 10.9 grams) was charged to the autoclave, heated to 90° C., then 1-hexadecene (3.9 grams, 5.0 milliliters) was added via syringe. Hydroformylation was conducted as in Example 30. In this case, the discharged reaction mixture was two phases. The bottom phase was highly colored, indicative of the catalyst, and the top phase was faintly yellow colored solid. The reaction was treated and analyzed as in Example 31. The reaction must be discharged from the autoclave warm (>40° C.), since the product solidifies upon cooling to ambient temperature. The results from hydroformylation and rhodium analysis are summarized in Table E.

EXAMPLE 33

A catalyst solution was prepared with 10.1 milligrams of dicarbonylacetylacetonato rhodium (I) (360 ppm), and 0.614 grams of Ligand A, and 9.80 grams of adiponitrile. The catalyst (10 milliliters, 9.5 g) was charged to the autoclave, heated to 90° C., then 1-dodecene (3.8 grams, 5.0 milliliters) was added via syringe. Hydroformylation was conducted as in Example 30. The discharged reaction mixture was two phases. The bottom phase was highly colored, indicative of the catalyst, and the top phase was faintly yellow. The reaction was treated and analyzed as in Example 31. The results from hydroformylation and rhodium analysis are summarized in Table E.

EXAMPLE 34

A catalyst solution was prepared with 16.3 milligrams of dicarbonylacetylacetonato rhodium (I) (325 ppm), and 0.719 grams of Ligand A, and 12.50 grams of tetramethylene sulfone (sulfolane). The catalyst (10 milliliters, 12.6 g) was charged to the autoclave, then heated to 90° C., then 1-hexadecene (3.9 grams, 5.0 milliliters) was added via syringe. Hydroformylation was conducted, is in Example 30. In this case, the discharged reaction mixture was two phases and was treated and analyzed as in Example 31. At ambient temperature, the bottom polar phase was burnt orange in color, indicative of the catalyst, and the top nonpolar phase was a slightly yellow solid. The results from hydroformylation and rhodium analysis are summarized in Table E.

EXAMPLE 35

A catalyst solution was prepared with 3.4 milligrams of dicarbonylacetylacetonato rhodium (I) (125 ppm), and 0.667 grams of Ligand A, and 10.2 grams of acetonitrile. The catalyst (11.8 milliliters, 9.20 g) was charged to the autoclave, heated to 90° C., then 1-tetradecene (2.5 grams, 3.2 milliliters) was added via syringe. Hydroformylation was conducted as in Example 30. In this case, the discharged reaction mixture was one phase at room temperature. Addition of hexanes created a dark burnt orange catalyst phase and a colorless top phase. The reaction was treated and analyzed as in Example 31. The results from hydroformylation and rhodium analysis are summarized in Table E.

EXAMPLE 36

A catalyst solution was prepared with 24.1 milligrams of dicarbonylacetylacetonato rhodium (I) (396 ppm), and 3.14 grams of Ligand A, and 21.1 grams of acetonitrile. The catalyst solution (12.0 milliliters, 9.6 grams) and 1-dodecene (5 milliliters, 3.791 milliliter, 22.5 mmol) were added to the autoclave at ambient temperature. The reaction was then heated to 100° C. The pressure in the autoclave was adjusted to 30 psi with nitrogen, then 80 psi of 1:1 syn gas was added to the autoclave. Hydroformylation was then conducted as in Example 30. In this case, the discharged reaction mixture was cone phase at room temperature. Addition of hexanes created a yellow-orange catalyst phase and a colorless top phase. The reaction was treated and analyzed as in Example 31. The results from hydroformylation and rhodium analysis are summarized in Table E.

EXAMPLE 37

A catalyst solution was prepared with 30.1 milligrams of dicarbonylacetylacetonato rhodium (I) (334 ppm), and 2.97 grams of Ligand A, and 32.9 grams of acetonitrile. The catalyst solution (11.75 milliliter, 9.3 grams) 1-dodecene (5 milliliters, 3.79 milliliters, 22.5 mmol) were added to the autoclave at ambient temperature. The reaction was then heated to 95° C. The pressure in the autoclave was adjusted to 40 psi with nitrogen, 10 psi of hydrogen was added, followed by 60 psi of syn gas. Hydroformylation was then conducted as in Example 30 with 1:1 syn gas as makeup. Addition of hexanes created a yellow-orange catalyst phase (bottom) and a colorless top phase. The reaction was treated and analyzed as in Example 31. The results from hydroformylation and rhodium analysis are summarized in Table E.

EXAMPLE 38

A catalyst solution was prepared with 24.1 milligrams of dicarbonylacetylacetonato rhodium (I) (396 ppm), and 3.14 grams of Ligand A, and 21.1 grams of acetonitrile. The catalyst solution (12.0 milliliters, 9.7 grams) 1-dodecene (5 milliliter, 3.79 milliliters, 22.5 mmol) were added to the autoclave at ambient temperature. The reaction was then heated to 100° C. The pressure in the autoclave was adjusted to 50 psi with nitrogen. Then 20 psi of hydrogen was added to the autoclave, followed by 40 psi of syn gas. Hydroformylation was then conducted as in Example 30 with 1:1 syn gas as makeup. Addition of hexanes created a yellow-orange catalyst phase (bottom) and a colorless top phase. The reaction was treated and analyzed as in Example 31. The results from hydroformylation and rhodium analysis a re summarized in Table E.

EXAMPLE 39

A catalyst solution was prepared with 15.8 milligrams of dicarbonylacetylacetonato rhodium (I) (404 ppm), and 1.03 grams of Ligand B, and 14.7 grams of acetonitrile. The catalyst (11.5 milliliters, 9.0 g) and 1-dodecene (3.8 grams, 5.0 milliliters) were charged to the autoclave at ambient temperature. The reaction was then heated to 90° C. Hydroformylation was conducted as in Example 30. The reaction mixture discharged from the autoclave was one phase at ambient temperature. Addition of hexanes created a yellow-orange catalyst phase and a colorless top phase. The reaction was treated and analyzed as in Example 31. The results from hydroformylation and rhodium analysis are summarized in Table E.

EXAMPLE 40

A catalyst solution was prepared with 13.1 milligrams of dicarbonylacetylac onto rhodium (I) (335 ppm), and 1.28 grams of Ligand B, and 14.4 grams of acetonitrile. The catalyst solution (11.5 milliliters, 8.9 grams) 1-dodecene (5 milliliters, 3.79 milliliter, 22.5 mmol) were added to the autoclave. The reaction was then heated to 95° C. The pressure in the autoclave was adjusted to 40 psi with nitrogen, 10 psi of hydrogen was added to the autoclave, followed by 60 psi of syn gas. Hydroformylation was then conducted of in Example 30 with 1:1 syn gas as makeup. Addition of hexanes created a yellow-orange catalyst phase (bottom) and a colorless top phases. The reaction was treated and analyzed as in Example 31. The results from hydroformylation and rhodium analysis are summarized in Table E.

EXAMPLE 41

A catalyst solution was prepared with 10.4 milligrams of dicarbonylacetylacetonato rhodium (I) (267 ppm), and 1.36 grams of Ligand B, and 14.3 grams of acetonitrile. The catalyst solution (11.5 milliliters, 9.1 grams) and 1-dodecene (5.0 milliliters., 3.79 milliliter, 22.5 mmol) were added to the autoclave. The reaction was then heated to 100° C. The pressure in the autoclave was adjusted to 50 psi with nitrogen, 20 psi of hydrogen was added to the autoclave, followed by 40 psi of syn gas. Hydroformylation was then conducted as in Example 30 with 1:1 syn gas as makeup. Addition of hexanes created a yellow-orange catalyst phase (bottom) and a colorless top phase. The reaction was treated and analyzed as in Example 31. The results from hydroformylation and rhodium analysis are summarized in Table E.

EXAMPLE 42

A catalyst solution was prepared with 9.1 milligrams of dicarbonylacetylacetonato rhodium (I) (319 ppm), and 0.585 grams of Ligand D, and 10.77 grams of dimethylformamide (DMF). The catalyst solution (10.7 grams, 11.3 milliliters) was charged to the autoclave, heated to 100° C., and then of 1-tetradecene (3.6 grams, 3.7 milliliters) was added via syringe. Hydroformylation was conducted as in Example 30. The discharged reaction mixture remained one phase at ambient temperature. The solution was then treated and analyzed as in Example 31. Initial phase separation with hexane created a dark brown polar phase (bottom) and a colorless nonpolar phase (top). The results from hydroformylation and rhodium analysis are summarized in Table E.

EXAMPLE 43

A catalyst solution was prepared with 16.3 milligrams of dicarbonylacetylacetonato rhodium (I) (390 ppm), and 0.552 grams of Ligand E, and 11.9 grams of DMSO. The catalyst (10 milliliters, 10.9 g) was charged to the autoclave, heated to 90° C., then 1-decene (3.7 grams, 5.0 milliliters) was added via syringe. Hydroformylation was conducted as in Example 30, with only one charge of olefin. In this case, the discharged reaction mixture was two phases and the reaction was treated and analyzed as in Example 31. The bottom polar phase was bright yellow in color, indicative of the catalyst, and the top nonpolar phase was colorless. The results from hydroformylation and rhodium analysis are summarized in Table E.

EXAMPLE 44

A catalyst solution was prepared with 6.3 milligrams of dicarbonylacetylacetonato rhodium (I) (300 ppm), and 94 milligrams of Ligand F, and 8.3 grams of acetonitrile. The catalyst solution (10 milliliters, 7.8 grams) and 1-dodecene (5.0 milliliters, 22 mmol) were added to the autoclave. The reaction was then heated to 90° C. Hydroformylation was conducted as in Example 30. In this case, the discharged reaction mixture was one phase at room temperature. After phase separation with hexane, the bottom phase was faint yellow and the top phase was colorless. The reaction was treated and analyzed as in Example 31. The results from hydroformylation and rhodium analysis are summarized in Table E.

EXAMPLE 45

A catalyst solution was prepared with 6.5 milligrams of dicarbonylacetylacetonato rhodium (I) (250 ppm), and 494 milligrams of Ligand G, and 9.9 grams of acetonitrile. The catalyst solution (10 milliliters, 7.8 grams) and 1-dodecene (5.0 milliliters, 22 mmol) were added to the autoclave. The reaction was then heated to 90° C. Hydroformylation was conducted as in Example 30. In this case, the discharged reaction mixture was one phase at room temperature. After phase separation with hexane, the bottom phase was yellow and the top phase was colorless. The reaction was treated and analyzed as in Example 31. The results from hydroformylation and rhodium analysis are summarized in Table E.

EXAMPLE 46

A catalyst solution was prepared with 6.4 milligrams of dicarbonylacetylacetonato rhodium (I) (250 ppm), and 440 milligrams of Ligand H, and 9.0 grams of acetonitrile. The catalyst solution (10 milliliters, 7.8 grams) and 1-dodecene (5.0 milliliters, 22 mmol) were added to the autoclave. The reaction was then heated to 90° C. Hydroformylation was conducted as in Example 30. In this case, the discharged reaction mixture was one phase at room temperature. After phase separation with hexane, the bottom phase was yellow and the top phase was colorless. The reaction was treated and analyzed as in Example 31. The results from hydroformylation and rhodium analysis are summarized in Table E.

Comparative Example O

A catalyst solution was prepared with 7.7 milligrams of dicarbonylacetylacetonato rhodium (I) (320 ppm), 0.391 grams of triphenylphosphine (TPP), and 9.29 grams of acetonitrile. The catalyst solution (9.20 grams, 11.7 milliliters) was charged to the autoclave, heated to 90° C., of 1-dodecene (2.5 grams, 3.3 milliliters) was added via syringe. Hydroformylation was conducted as in Example 30. After the initial charge of olefin was consumed, a second aliquot of 1-dodecene (2.5 grams, 3.1 milliliters) was added via syringe. The one phase reaction phase separated as in Example 31. After the initial phase separation with hexane, both of the phases were nearly equally yellow in color. The top nonpolar phase was carefully separated from the polar phase. The nonpolar phase was washed 3 times with an equal amount of acetonitrile (10 percent by weight of the initial weight of the nonpolar phase). A very distinct yellow color remained in the nonpolar after washing with acetonitrile, indicating a significant portion of rhodium still in the nonpolar phase. The results from hydroformylation and rhodium analysis are summarized in Table E.

Comparative Example P

A catalyst solution was prepared with 8.6 milligrams of dicarbonylacetylacetonato rhodium (I), 0.655 grams of triphenylphosphine (TPP), and 12.8 grams of dimethyl sulfoxide (DMSO). The catalyst (10.7 milliliters, 12.2 grams)

was charged to the autoclave, heated to 90° C., then 1-tetradecene (3.3 grams, 4.3 milliliters) was added via syringe. Hydroformylation was then conducted as in Example 30. The reaction discharged from the autoclave in two phases. The reaction mixture was treated and analyzed as in Example 31. After adding hexane to the phase separated reaction mixture and allowing the reaction to stand for four days, the bottom phase was highly colored and the top phase maintained a distinct color, indicative rhodium catalyst remaining in the nonpolar phase. The results from hydroformylation and rhodium analysis are summarized in Table E.

Comparative Example Q

A catalyst solution was prepared with 10.3 milligrams of dicarbonylacetylacetonato rhodium (I), 0.246 grams of cyclohexyldiphenylphosphite (CHDPP), and 12.6 grams of DMF. The catalyst (12.8 milliliters, 12.1 grams) was charged to the autoclave, heated to 90° C., then 1-tetradecene (3.4 grams, 4.3 milliliters) was added via syringe. Hydroformylation was then conducted as in Example 30. The one phase reaction mixture was treated and analyzed as Example 31. After allowing the reaction to stand for four days, the bottom phase was highly colored and the top phase (nonpolar phase) maintained a distinct orange tint. The results from hydroformylation and rhodium analysis are summarized in Table E.

TABLE E

| Example # | Ligand | Initial Rate (seconds) | N/I | Rh (ppb) in nonpolar phase | Rh (ppm) in the polar phase |
| --- | --- | --- | --- | --- | --- |
| 30 | A | 39 | 7.5 | 241 | 385 |
| 31 | A | 270 | 8/20** | 86 | 341 |
| 32 | A | 390 | 8*/19** | 39 | 324 |
| 33 | A | 950 | 15*/36** | 329 | 343 |
| 34 | A | 260 | 14*/11** | 494 | 355 |
| 35 | A | 1600 | 8.6 | 404 | 214 |
| 36 | A | 60 | 10 | 359 | 344 |
| 37 | A | 55 | 15 | 164 | 321 |
| 38 | A | 120 | 14 | 277 | 347 |
| 39 | B | 30 | 8 | 425 | 273 |
| 40 | B | 55 | 10.5 | 474 | 345 |
| 41 | B | 95 | 8 | 134 | 252 |
| 42 | D | 45 | 5.5 | 759 | 320 |
| 43 | E | 33 | 2.5*/2.5** | 763 | 544 |
| 44 | F | 24 | 3 | 3,000 | — |
| 45 | G | 420 | 4.4 | 6,000 | 236 |
| 46 | H | 20 | 5 | 20,000 | 226 |
| Comparative O | TPP | 14 | 5 | 75,000 | — |
| Comparative P | TPP | 20 | 7**/7** | 44,000 | 220 |
| Comparative Q | CHDPP | 23 | 3 | 79,000 | 226 |

*N/I in the nonpolar phase
**N/I in the polar phase

The above Examples show that appropriate polarity ligands provide high rhodium recovery via a single extraction with hexane.

EXAMPLE 47

A catalyst solution was prepared with 8.7 milligrams of dicarbonylacetylacetonato rhodium (I) (320 parts per million), 0.570 grams of Ligand A, and 10.36 grams of acetonitrile. The catalyst solution (9.1 grams, 11.7 milliliters) was charged to a 100 milliliter autoclave (equipped with a magnetically coupled stirrer), then solution was heated to 90° C. under 1 atmosphere of nitrogen. Upon reaching temperature, 2.5 grams of 1-dodecene (3.3 milliliters) were added to the autoclave. Hydroformylation was performed as in Example 30. After the rate slowed significantly from the initial rate (>400 seconds for a 5 psi drop), an additional of 3.0 grams of olefin (4.0 milliliters) were charged to the autoclave. Gas consumption was; measure until no further gas uptake was observed. The discharged reaction mixture remained one phase at room temperature. GC analysis indicated nearly complete consumption of the α-olefin. Table F outlines the results from the hydroformylation. An equal amount by weight of hexanes was then added to the reaction solution to cause phase separation. After shaking then allowing the solution to phase separate, an orange bottom phase and a colorless top phase were observed. GC analysis determined the top layer to be the nonpolar phase and the bottom layer to be the polar phase. The phase-separated material was allowed to stand for approximately 30 minutes, then the phases were separated via a separatory funnel. The top phase was weighed, then was washed 3 times with acetonitrile (10 weight percent of the nonpolar phase). Each wash consisted of adding the acetonitrile, shaking vigorously, and then allowing, the mixture to settle for approximately 30 minutes. The results from hydroformylation and rhodium analysis are summarized in Table F.

EXAMPLE 48

A catalyst solution prepared with 7.8 milligrams of dicarbonylacetylacetonato rhodium (I) (320 parts per million), 0.512 grams of Ligand A, and 10.36 grams of acetonitrile. The catalyst (11.7 milliliters, 9.2 grams) was charged to the autoclave, heated to 90° C., then 1-decene (2.5 grams, 3.3 milliliters) was added via syringe. Hydroformylation was conducted as in Example 30. The reaction was conducted at 90° C. with 80 psi of syn gas. After the initial reaction slowed, a second aliquot of 1-decene (3.0 grams, 4.0 milliliters) was added via syringe. The discharged reaction mixture was one phase and was treated and analyzed as in Example 47. After the initial phase separation with hexane, the upper phase was virtually colorless and the lower phase was yellow orange. The results from hydroformylation and rhodium analysis are summarized in Table F.

EXAMPLE 49

A catalyst solution was prepared with 7.8 milligrams of dicarbonylacetylacetonato rhodium (I) (320 parts per million), 0.511 grams of Ligand A, and 9.30 grams of acetonitrile. The catalyst solution (11.7 milliliters, 9.2 grams) was charged to the autoclave, heated to 90° C., then 1-tetradecene (2.5 grams, 3.2 milliliters) was added via syringe. Hydroformylation was conducted as in Example 30. After the initial reaction slowed, a second aliquot of 1-tetradecene (3.1 grams, 4.0 milliliters) was added via syringe. The discharged reaction mixture was one phase and was treated and analyzed as, in Example 47. After the initial phase separation with hexane, the upper phase was virtually colorless and the lower phase was yellow orange. The results from hydroformylation and rhodium analysis are summarized in Table F.

EXAMPLE 50

A catalyst solution was prepared with 7.8 milligrams of dicarbonylacetylacetonato rhodium (I) (320 ppm), 0.511 grams of Ligand A, and 9.30 grams of acetonitrile. The catalyst solution (11.7 milliliters, 9.2 grams) was charged to the autoclave, heated to 90° C., then 1-hexadecene (2.5 grams, 3.2 milliliters) was added via syringe. Hydroformylation was conducted as in Example 30. After the initial reaction slowed, a second aliquot of 1-hexadecene (3.1 grams, 4.0 milliliters) was added via syringe. The discharged reaction mixture was two phases and maintained two phase up to about 45° C. Each phase was analyzed by GC. In this case, the slightly yellow lower phase contained the product and the highly colored the phase was the polar acetonitrile phase, which contained the ligand/catalyst. An equal amount by weight of hexanes was then added to the reaction, then the reaction was treated and analyzed as in Example 47. The results from hydroformylation and rhodium analysis are summarized in Table F. Note: the reaction must be discharged from the autoclave warm (about 50° C.), since the product will solidify upon cooling to room temperature. The results are summarized in Table F.

EXAMPLE 51

A catalyst solution was prepared with 9.8 milligrams of dicarbonylacetylacetonato rhodium (I) (320 ppm), 0.641 grams of Ligand A, and 11.64 grams of dimethylformamide (DMF). The catalyst (11.2 milliliters, 11.2 grams) was charged to the autoclave, heated to 90° C., then 1-dodecene (2.9 grams, 3.8 milliliters) was added via syringe. Hydroformylation was conducted as in Example 30. After the initial reaction slowed, a second aliquot of 1-dodecene (3.0 grams, 4.0 milliliters) was added via syringe. The discharged reaction mixture was one phase and was treated and analyzed as in Example 47. After the initial phase separation with hexane, the upper phase was virtually colorless and the lower phase was dark brown. The results from hydroformylation and rhodium analysis are summarized in Table F.

EXAMPLE 52

A catalyst solution was prepared with 9.8 milligrams of dicarbonylacetylacetonato rhodium (I) (320 parts per million), 0.641 grams of Ligand A, and 11.61 grams of epsilon caprolactone. The catalyst (10.9 milliliters, 11.4 grams) was charged to the autoclave, heated to 90° C., then 1-dodecene (3.2 grams, 4.1 milliliters) was added via syringe. Hydroformylation was conducted as in Example 30. After the initial reaction slowed, a second aliquot of 1-dodecene (3.1 grams, 4.0 milliliters) was added via syringe. The discharged reaction mixture was one phase and was treated and analyzed as in Example 47. After the initial phase separation with hexane, the upper phase was virtually colorless and the lower phase was orange brown. The results from hydroformylation and rhodium analysis are summarized in Table F.

EXAMPLE 53

A catalyst solution was prepared with 6.3 milligrams of dicarbonylacetylacetonato rhodium (I) (292 parts per million), 90 milligrams of Ligand C, and 8.5 grams of acetonitrile. The catalyst solution (8.5 grams, 10 milliliters) and 1-dodecene (3.8 grams, 5.0 milliliters) were charged to the autoclave at ambient temperature. The reaction was then heated to 90° C. Hydroformylation, was then conducted as in Example 30. A second charged of olefin was not added to the reaction. The discharged reaction mixture remained one phase at ambient temperature. The solution was then treated and analyzed as in Example 47. Initial phase separation with hexane created a bright orange polar phase (bottom) and a colorless nonpolar phase (top). The results from hydroformylation and rhodium analysis are summarized in Table F.

TABLE F

| Example # | Ligand | Initial Rate (seconds) | N/I | Rh (ppb) in non-polar phase after 3 extractions with acetonitrile | Rhodium (ppm)* |
|---|---|---|---|---|---|
| 47 | A | 51 | 7.5 | 287 | 311 |
| 48 | A | 39 | 7.7 | 24 | — |
| 49 | A | 51 | 7.4 | 158 | 324 |
| 50 | A | 77 | 7.8 | 427 | 343 |
| 51 | A | 48 | 6.4 | 55 | 390 |
| 52 | A | 51 | 6.6 | 114 | — |
| 53 | C | 320 | 48 | 1,200 | 300 |

EXAMPLE 54

A catalyst solution was prepared with 10.5 milligrams of dicarbonylacetylacetonato rhodium (I) (320 parts per million), 0.686 grams of Ligand A, and 12.5 grams of 3-methyl-2-oxazolidinone. The catalyst (10.7 milliliters, 12.6 grams) was charged to the autoclave, heated to 90° C., then 1-dodecene (3.5 grams, 4.3 milliliters) was added via syringe. Hydroformylation was conducted as in Example 30. After the initial reaction slowed, a second aliquot of 1-dodecene (3.1 grams, 4.0 milliliters) was added via syringe. The discharged reaction mixture was two phases and maintained two phases up to reaction temperature. GC analysis determined the dark brown bottom phase to be the polar catalyst layer and the faintly colored top phase to be aldehyde layer. Rhodium content was determined for the top product phase via ICP. The results from hydroformylation and rhodium analysis are summarized in Table G.

EXAMPLE 55

A catalyst solution was prepared with 10 milligrams of dicarbonylacetylacetonato rhodium (I) (320 parts per million), 0.654 grams of Ligand A, and 11.9 grams of dimethyl sulfoxide. The catalyst (10.7 milliliters, 12.1 grams) was charged to the autoclave, heated to 90° C., then 1-dodecene (3.3 grams, 4.3 milliliters) was added via syringe. Hydroformylation was conducted as in Example 30. After the initial reaction slowed, a second aliquot of 1-dodecene (3.1 grams, 4.0 milliliters) was added via syringe. The discharged reaction mixture was two phases and maintained two phases up to reaction temperature. GC analysis determined the dark brown bottom phase to be the polar catalyst layer and the faintly colored top phase to be aldehyde layer. Rhodium content was determined for the top product phase via ICP. The results from hydroformylation and rhodium analysis are summarized in Table G.

EXAMPLE 56

A catalyst solution was prepared with 9.5 milligrams of dicarbonylacetylacetonato rhodium (I) (320 parts per million), 0.620 grams of Ligand A, and 11.3 grams of adiponitrile. The catalyst (11.2 milliliters, 10.8 grams) was charged to the autoclave, heated to 90° C., then 1-dodecene (2.9 grams, 3.8 milliliters) was added via syringe. Hydroformylation was conducted as in Example 30. After the initial reaction slowed, a second aliquot of 1-dodecene (3.0 grams, 4.0 milliliters) was added via syringe. The discharged reaction mixture was two phases and maintained two phases at 80° C. GC analysis determined the orange bottom phase to be the polar catalyst layer and the faintly colored top phase to be aldehyde layer. Rhodium content was determined for the top product phase via ICP. The results from hydroformylation and rhodium analysis are summarized in Table G.

TABLE G

| Example # | Ligand | Initial Rate (seconds) | N/I | Rh (ppb) in product phase | Rhodium (ppm) in the polar phase |
|---|---|---|---|---|---|
| 54 | A | 140 | 7.7*/7.1** | 6,000 | 306 |
| 55 | A | 140 | 7.9*/7.3** | 7,000 | — |
| 56 | A | 260 | 10.9*/11.7** | 9,000 | — |

*N/I in the nonpolar phase
**N/I in the polar phase

EXAMPLE 57

A catalyst solution was prepared containing 97 parts per million by weight of rhodium, 0.09 percent by weight of Ligand R and acetonitrile (as the solvent) was charged to a 100 milliliter stainless steel autoclave at 74° C. To this solution was then charged 5 milliliters of 1-dodecene. The solution was stirred and allowed to equilibrate until no increase in pressure was observed. The reactor was then pressurized to 100 psig with $H_2$:CO (1:1). Pressure was maintained between 100 and 95 psig until no further reaction had occurred. At this point, the catalyst containing solution was discharged from the reactor. 1.5 milliliters of the catalyst solution was transferred to a vial. To this was added 1.5 milliliters of hexane. The mixture was vigorously shaken for several minutes, then allowed to settle and phase separate. The layers were then separated and analyzed for rhodium content. Kpartition in this mixture was found to be 5.3.

EXAMPLE 58

A catalyst solution was prepared with 21.3 milligrams of dicarbonylacetylacetonato rhodium (I) (520 parts per million), 0.172 grams of Ligand K, 8.11 grams of DMSO, and 8.1 grams of undecanol. The catalyst (20.0 milliliters, 18.8 grams) and 1-dodecene (3.8 grams, 5.0 milliliters) was charged to the autoclave, then heated to 90° C. Upon equilibrating at temperature, 500 psi of 1:1 hydrogen:carbon monoxide was added to the reactor. After approximately 1.5 hours the reactor was cooled and vented. The discharged reaction mixture was bright yellow and one phase at room temperature. GC analysis of the reaction mixture indicated about a 2 to 1 ratio of aldehydes (N/I of 1.7) to alcohols (N/I of 6.2). 5.0 grams of hexane was added to 5.0 grams of the catalyst solution. The solution was shaken vigorously then allowed to settle for a number of days. The resulting solution had two phases. The lower phase was dark yellow and contained 1724 parts per million rhodium; whereas the top phase was clear and colorless and contained 5.4 parts per million rhodium. The ratio of the top phase to bottom phase by volume was about 15 to 1.

EXAMPLE 59

A vial was charged with 3.0 grams of acetonitrile, 3.0 grams of hexane, and 1.0 grams of pentadecanal. The pentadecanal was obtained from a hydroformylation reaction with 1-tetradecene and consisted of iso- pentadecanal, n- pentadecanal, and a small amount of $C_{14}$ alkenes and $C_{14}$ alkanes. The vial was shaken vigorously, then allowed to settle. An aliquot from both phases was removed and analyzed for aldehyde via GC. Table H indicates the partition coefficient, which was determined by the ratio of the GC area for the aldehydes (sum of n and iso) in the nonpolar phase to the polar phase.

EXAMPLE 60

Example 59 was repeated using heptadecanal in place of pentadecanal. In this case, the aldehyde contained iso-heptadecanal, n-heptadecanal, and a small amount of $C_{16}$ alkenes and alkanes. Table H indicates the partition coefficient.

EXAMPLE 61

Example 59 was repeated using a 3:3:1 ratio (by weight) of undecanal, 2,2-dimethylbutane, and acetonitrile. Table H indicates the partition coefficient.

EXAMPLE 62

Example 59 was repeated using a 3:3:1 ratio (by weight) of dodecanal, 2,2-dimethylbutane, and acetonitrile. Table H indicates the partition coefficient.

EXAMPLE 63

Example 59 was repeated using a 3:3:1 ratio (by weight) of undecanal, cyclohexane, and acetonitrile. Table H indicates the partition coefficient.

EXAMPLE 64

Example 59 was repeated using a 3:3:1 ratio (by weight) of dodecanal, heptane, and acetonitrile. Table H indicates the partition coefficient.

EXAMPLE 65

Example 59 was repeated using a 3:3:1 ratio (by weight) of undecanal, nonane, and acetonitrile. Table H indicates the partition coefficient.

EXAMPLE 66

Example 59 was repeated using a 3:3:1 ratio (by weight) of undecanal, 1-decene, and acetonitrile. Table H indicates the partition coefficient.

EXAMPLE 67

Example 59 was repeated using a 3:3:1 ratio (by weight) of tridecanal, 1-dodecene, and acetonitrile. The tridecanal was obtained from a hydroformylation reaction with 1-dodecene and consisted of iso- tridecanal, n- tridecanal, and a small amount of $C_{12}$ alkenes and $C_{12}$ alkanes. Table H indicates the partition coefficient.

EXAMPLE 68

Example 59 was repeated using a 3:3:1 ratio (by weight) of undecanal, hexane, and 3-methyl-2-oxazolidinone. Table H indicates partition coefficient.

TABLE H

| Example | Aldehyde | Solvents | Kpartition |
|---|---|---|---|
| 59 | pentadecanal | hexane/acetonitrile | 6.8 |
| 60 | heptadecanal | hexane/acetonitrile | 5.5 |
| 61 | undecanal | 2,2-dimethylbutane/acetonitrile | 3.3 |
| 62 | dodecanal | 2,2-dimethylbutane/acetonitrile | 4.6 |

TABLE H-continued

| Example | Aldehyde | Solvents | Kpartition |
|---|---|---|---|
| 63 | undecanal | cyclohexane/acetonitrile | 2.0 |
| 64 | dodecanal | heptane/acetonitrile | 4.4 |
| 65 | undecanal | nonane/acetonitrile | 1.9 |
| 66 | undecanal | 1-decene/acetonitrile | 2.3 |
| 67 | tridecanal | 1-dodecene/acetonitrile | 4.3 |
| 68 | undecanal | hexane/3-methyl-2-oxazolidinone | 2.6 |

EXAMPLE 69

To a solution containing 0.1 percent by weight of Ligand S depicted below in acetonitrile was added an equal volume of hexane. The mixture was vigorously shaken for several minutes then allowed to settle and phase separate. The amount of Ligand S in each phase was then determined. The Kpartition was greater than 100.

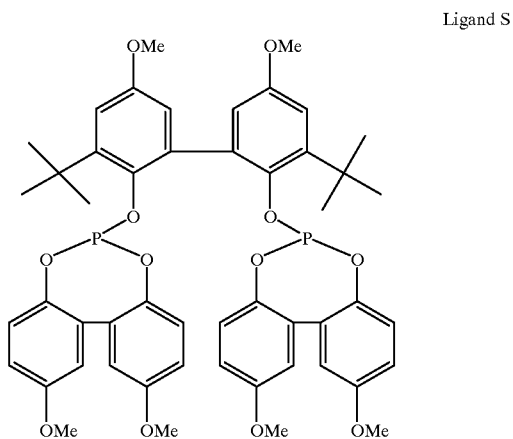

Ligand S

Although the invention has been illustrated by certain of the preceding examples, it is not to be construed as being limited thereby; but rather, the invention encompasses the generic area as hereinbefore disclosed. Various modifications and embodiments can be made without departing from the spirit and scope thereof.

We claim:

1. A process for separating one or more products from a reaction product fluid comprising a metal-organophosphorus ligand complex catalyst, optionally free organophosphorus ligand, a nonpolar solvent, a polar solvent and said one or more product, wherein said process comprises (1) mixing said reaction product fluid to obtain by phase separation a polar phase comprising said metal-organophosphorus ligand complex catalyst, optionally free organophosphorus ligand and said polar solvent and in nonpolar phase comprising said one or more products and nonpolar solvent, and (2) recovering said nonpolar phase from said polar phase; wherein said organophosphorus ligand has a partition coefficient between the polar solvent and the nonpolar solvent of greater than about 10, and said one or more products have a partition coefficient between the nonpolar solvent and the polar solvent of greater than about 0.5.

2. A process for separating one or more products from a reaction product fluid comprising a metal-organophosphorus ligand complex catalyst, optionally free organophosphorus ligand, a polar solvent and said one or more products, wherein said process comprises (1) mixing said reaction product fluid with a nonpolar solvent to obtain by phase separation a polar phase comprising said metal-organophosphorus ligand complex catalyst, optionally free organophosphorus ligand and said polar solvent and a nonpolar phase comprising said one or more products and nonpolar solvent, and (2) recovering said nonpolar phase from said polar phase; wherein said organophosphorus ligand has a partition coefficient between the polar solvent and the nonpolar solvent of greater than about 10, and said one or more products have a partition coefficient between the nonpolar solvent and the polar solvent of greater than about 0.5.

3. A process for producing one or more products comprising: (1) reacting one or more reactants in the presence of a metal-organophosphorus ligand complex catalyst, optionally free organophosphorus ligand, a polar solvent and a nonpolar solvent to form a multiphase reaction product fluid; and (2) separating said multiphase reaction product fluid to obtain one phase comprising said one or more reactants, metal-organophosphorus ligand complex catalyst, optionally free organophosphorus ligand and polar solvent and at least one other phase comprising said one or more products and nonpolar solvent; wherein said organophosphorus ligand has a partition coefficient between the polar solvent and the nonpolar solvent of greater than about 10, and said one or more products have a partition coefficient between the nonpolar solvent and the polar solvent of greater than about 0.5.

4. A process for producing one or more products comprising: (1) reacting one or more reactants in the presence of a metal-organophosphorus ligand complex catalyst, optionally free organophosphorus ligand and a polar solvent to form a reaction product fluid; (2) mixing said reaction product fluid with a nonpolar solvent to form a multiphase reaction product fluid; and (3) separating said multiphase reaction product fluid to obtain one phase comprising said one or more reactants, metal-organophosphorus ligand complex catalyst, optionally free organophosphorus ligand and polar solvent and at least one other phase comprising said one or more products and nonpolar solvent; wherein said organophosphorus ligand has a partition coefficient between the polar solvent and the nonpolar solvent of greater than about 10, and said one or more products have a partition coefficient between the nonpolar solvent and the polar solvent of greater than about 0.5.

5. The process of claim 3 comprising: (1) reacting an olefinic unsaturated compound with carbon monoxide and hydrogen in the presence of a metal-organophosphorus ligand complex catalyst, optionally free organophosphorus ligand, a polar solvent and a nonpolar solvent to form a multiphase reaction product fluid; and (2) separating said multiphase reaction product fluid to obtain one phase comprising said olefinic unsaturated compound, metal-organophosphorus ligand complex catalyst, optionally free organophosphorus ligand and polar solvent and at least one other phase comprising said aldehydes and nonpolar solvent; wherein said organophosphorus ligand has a partition coefficient between the polar solvent and the nonpolar solvent of greater than about 10, and said aldehydes have a partition coefficient between the nonpolar solvent and the polar solvent of greater than about 0.5.

6. The process of claim 4 comprising: (1) reacting an olefinic unsaturated compound with carbon monoxide and hydrogen in the presence of a metal-organophosphorus ligand complex catalyst, optionally free organophosphorus ligand and a polar solvent to form a reaction product fluid; (2) mixing said reaction product, fluid with a nonpolar solvent to form a multiphase reaction product fluid; and (3) separating said multiphase reaction product fluid to obtain one phase comprising said olefinic unsaturated compound, metal-organophosphorus ligand complex catalyst, optionally free organophosphorus ligand and polar solvent and at least one other phase comprising said aldehydes and non-polar solvent; wherein said organophosphorus ligand has a partition coefficient between the polar solvent and the non-polar solvent of greater than about 10, and said aldehydes have a partition coefficient between the nonpolar solvent and the polar solvent of greater than about 0.5.

7. The process of claim 1 wherein said organophosphorus ligand has a partition coefficient between the polar solvent and the nonpolar solvent of greater than about 15.

8. The process of claim 2 wherein said organophosphorus ligand has a partition coefficient between the polar solvent and the nonpolar solvent of greater than about 15.

9. The process of claim 1 wherein said one or more products have partition coefficient between the nonpolar solvent and the polar solvent of greater than about 0.75.

10. The process of claim 2 wherein said one or more products have a partition coefficient between the nonpolar solvent and the polar solvent of greater than about 0.75.

11. The process of claim 1 which comprises a hydroformylation, hydroacylation (intramolecular and intermolecular), hydrocyanation, hydroamidation, hydroesterification, aminolysis, alcoholysis, hydrocarbonylation, hydroxycarbonylation, carbonylation, isomerization or transfer hydrogenation process.

12. The process of claim 1 wherein said polar solvent is selected from nitriles, lactones, pyrrolidones, formamides and sulfoxides.

13. The process of claim 1 wherein said nonpolar solvent is selected from alkanes, cycloalkanes, alkenes, aldehydes, ketones, ethers, esters, amines, aromatics, silanes, silicones and carbon dioxide.

14. The process of claim 12 wherein said polar solvent is selected from propionitrile, 1,3-dioxolane, 3-methoxypropionitrile, N-methylpyrrolidone, N,N-dimethylformamide, 2-methyl-2-oxazoline, adiponitrile, acetonitrile, epsilon caprolactone, glutaronitrile, 3-methyl-2-oxazolidinone, dimethyl sulfoxide and sulfolane.

15. The process of claim 13 wherein said nonpolar solvent is selected from propane, 2,2-dimethylpropane, butane, 2,2-dimethylbutane, pentane, isopropyl ether, hexane, trimethylamine, heptane, octane, nonane, decane, isobutyl isobutyrate, tributylamine, undecane, 2,2,4-trimethylpentyl acetate, isobutyl heptyl ketone, diisobutyl ketone, cyclopentane, cyclohexane, isobutylbenzene, n-nonylbenzene, n-octylbenzene, n-butylbenzene, p-xylene, ethylbenzene, 1,3,5-trimethylbenzene, m-xylene, toluene, o-xylene, decene, docenene, tetradecene, and heptadecanal.

16. The process of claim 1 wherein said metal-organophosphorus ligand complex catalyst comprises rhodium complexed with an organophosphorus ligand represented by the formula:

(i) a triorganophosphine ligand represented by the formula:

wherein $R^1$ is the same or different and represents a substituted or unsubstituted monovalent hydrocarbon radical containing from 1 to 24 carbon atoms or greater;

(ii) a monoorganophosphite represented by the formula:

wherein $R^3$ represents a substituted or unsubstituted trivalent hydrocarbon radical containing from 4 to 40 carbon atoms or greater;

(iii) a diorganophosphite represented by the formula:

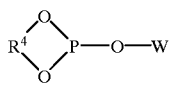

wherein $R^4$ represents a substituted or unsubstituted divalent hydrocarbon radical containing from 4 to 40 carbon atoms or greater and W represents a substituted or unsubstituted monovalent hydrocarbon radical containing from 1 to 18 carbon atoms or greater;

(iv) a triorganophosphite represented by the formula:

wherein each $R^8$ is the same or different and represents a substituted or unsubstituted monovalent hydrocarbon radical; and (v) an organopolyphosphite containing two or more tertiary (trivalent) phosphorus atoms represented by the formula:

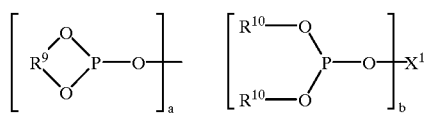

wherein $X^1$ represents a substituted or unsubstituted n-valent hydrocarbon bridging radical containing from 2 to 40 carbon atoms, each $R^9$ is the same or different and represents a divalent hydrocarbon radical containing from 4 to 40 carbon atoms, each $R^{10}$ is the same or different and represents a substituted or unsubstituted monovalent hydrocarbon radical containing from 1 to 24 carbon atoms, a and b can be the same or different and each have a value of 0 to 6, with the proviso that the sum of a+b is 2 to 6 and n equals a+b.

17. The process of claim 5 wherein said olefinic unsaturated compound comprises one or more pentenoic acids and/or salts and said aldehydes comprises one or more formylvaleric acids and/or salts.

18. The process of claim 6 wherein said olefinic unsaturated compound comprises one or more pentenoic acids and/or salts and said aldehydes comprise one or more formylvaleric acids and/or salts.

* * * * *